(12) United States Patent
Shock et al.

(10) Patent No.: US 7,598,494 B2
(45) Date of Patent: Oct. 6, 2009

(54) AUTOMATED FTIR GAS ANALYZER

(75) Inventors: Robert Shock, Meriden, CT (US);
Edward DesPlaines, Cheshire, CT (US);
Cliff Perdion, Cheshire, CT (US);
William Bertuleit, Berlin, CT (US); Joe Camardo, Newington, CT (US); Mike Cotteleer, West Chicago, IL (US);
James Gruenbacher, Meriden, CT (US); Richard Jacaruso, Baton Rouge, LA (US); Terry Paradis, Bristol, CT (US); Steve Weiss, Naugatuck, CT (US)

(73) Assignee: Airgas, Inc., Cheshire, CT (US)

( * ) Notice: Subject to any disclaimer, the term of this patent is extended or adjusted under 35 U.S.C. 154(b) by 382 days.

(21) Appl. No.: 11/699,856

(22) Filed: Jan. 30, 2007

(65) Prior Publication Data
US 2008/0179529 A1 Jul. 31, 2008

(51) Int. Cl.
*G01N 21/35* (2006.01)
(52) U.S. Cl. .................................................. 250/343
(58) Field of Classification Search ........................ None
See application file for complete search history.

(56) References Cited

U.S. PATENT DOCUMENTS

| | | | |
|---|---|---|---|
| 4,809,196 A | 2/1989 | Miller | |
| 5,507,192 A | 4/1996 | Beaudin | |
| 5,610,706 A | 3/1997 | Carroll et al. | |
| 5,739,038 A | 4/1998 | Burrows | |
| 5,970,804 A | 10/1999 | Robbat, Jr. | |
| 6,748,334 B1 | 6/2004 | Perez et al. | |
| 6,772,072 B2 | 8/2004 | Ganguli et al. | |
| 6,793,889 B2 | 9/2004 | Naatz et al. | |
| 7,472,023 B2 * | 12/2008 | Leu et al. | 702/27 |
| 2004/0035183 A1 | 2/2004 | O'Brien et al. | |

OTHER PUBLICATIONS

International Search Report dated May 27, 2008, application no. PCT/US2008/001141.

* cited by examiner

*Primary Examiner*—David P Porta
*Assistant Examiner*—Carolyn Igyarto
(74) *Attorney, Agent, or Firm*—Ratner Prestia

(57) ABSTRACT

A system for certifying a concentration of gas in a cylinder includes a gas cell configured to receive a sample gas from a cylinder, and an FTIR module coupled to the gas cell for scanning the sample gas and forming a beam spectrum. A processor is coupled to the FTIR module for calculating an intensity response of the sample gas based on the beam spectrum. A storage device is included for storing data points of a plot of intensity response of a known gas versus concentration levels. The processor is configured to interpolate between the stored data points of the plot to determine an interpolated data point corresponding to the intensity response of the sample gas. The processor provides to the user a concentration level of the sample gas, based on the interpolated data point.

10 Claims, 22 Drawing Sheets

PRESSURIZING CELL PRESSURE CTL [65535]
SCAN PRESSURE TARGET [1000]
BATCH SCAN TYPE [BLEED-THROUGH]

20

VENT CONTROL SETTINGS

VENT CONTROL VALVE TUNING

| CELL STABILIZATION ALGORITHM | PID |
| STABILIZATION CELL PRESSURE CTL | 30000 |
| ALGORITHM SWITCH PRESSURE | 990 |
| SCAN PRESSURE HIGH | 1000.2 |
| SCAN PRESSURE LOW | 999.8 |
| CELL STABILITY FACTOR | 0.0001 |

VENT PID_Gains
- GAIN: 100.000
- INTEGRAL: 0.001
- DERIVATIVE: 0.000
- max_EGU: 2586
- max_EGU2: 0
- min_EGU: 65535

VENT AUTOTUNING PARAMETERS
- controller_type: PID
- cycles_to_avg: 10
- relay_amplitude: 2
- control_design: NORMAL
- noise_level: 2.6 tuning_completed ○
dt: 0.001
AUTOTUNE ▶
REINITIALIZE ▶

ENVIRONICS CONTROL SETTINGS

ENVIRONICS CONTROL VALVE TUNING

| CELL STABILIZATION ALGORITHM | AutoTune PID |
| STABILIZATION CELL PRESSURE CTL | 25000 |
| ALGORITHM SWITCH PRESSURE | 1000 |
| SCAN PRESSURE HIGH | 1001 |
| SCAN PRESSURE LOW | 999 |
| CELL STABILITY FACTOR | 0.0005 |

ENVIRONICS PID_Gains
- GAIN: 100.000
- INTEGRAL: 0.010
- DERIVATIVE: 0.000
- max_EGU: 2586
- max_EGU2: 0
- min_EGU: 65535

ENVIRONICS AUTOTUNING PARAMETERS
- controller_type: PID
- cycles_to_avg: 10
- relay_amplitude: 2
- control_design: NORMAL
- noise_level: 2.6 tuning_completed ○
dt: 0.001
AUTOTUNE ▶
REINITIALIZE ▶

FIG. 3

AUTOMATED FTIR GAS ANALYZER

FIELD OF THE INVENTION

The present invention relates, in general, to a system and method for analyzing a gas contained in a cylinder and certifying its concentration level. More specifically, the present invention relates to analyzing a gas using an interferometer and a computer controlled gas cell environment, which are precisely controlled to accurately determine the concentration level of the gas in the cylinder.

BACKGROUND OF THE INVENTION

Specialty gas manufacturers are required to perform gas analysis and certification on all gas tanks shipped to a user. Consequently, every gas tank after being filled in the production area is moved to an analytical laboratory for certification by qualified personnel.

For many years, chemical spectroscopy in industrial settings was performed off-line from the production line, with samples being extracted and taken to an analytical laboratory for analysis and interpretation. This procedure often consumed hours or days before the results were reported back to the chemical process engineer or technician.

One chemical spectroscopy system, which is performed on-line with the production line, is disclosed by Perez et al., in U.S. Pat. No. 6,748,334 issued on Jun. 8, 2004. This U.S. patent describes Fourier Transform Infrared (FTIR) Spectroscopy which bases its functionality on the principle that molecules absorb infrared light. Only the monatomic (He, Ne, Ar, etc.) and homopolar diatomic ($H_2$, $N_2$, $O_2$, etc.) molecules do not absorb infrared light. Molecules only absorb infrared light at those frequencies where the infrared light affects the dipolar moment of the molecule. Molecules with a dipolar moment allow infrared photons to interact with the molecule causing excitation to higher vibrational states. The homopolar diatomic molecules do not have a dipolar moment, because the electric fields of its atoms are equal. Monatomic molecules do not have a dipolar moment because they only have one atom. Therefore, homopolar diatomic molecules and monatomic molecules do not absorb infrared light. But all other molecules do absorb infrared light.

FTIR spectroscopy generally uses a Michelson interferometer to spread a sample with the infrared light spectrum and measure the intensity of the infrared light spectrum which was not absorbed by the sample. FTIR spectroscopy observes all optical frequencies from the source simultaneously over a period of time known as a scan time.

The FTIR spectrometer measures the intensity of an infrared beam after it passes through a sample. The resulting signal, which is a time domain digital signal, is called an interferogram and contains intensity information about all frequencies present in the infrared beam. This information may be extracted by changing the signal from a time domain digital signal to a frequency domain digital signal. This change is accomplished by applying a Fourier transform over the interferogram and producing a spectral pattern known as a single beam spectrum.

Almost all molecules absorb infrared light, and each type of molecule only absorbs infrared light at certain frequencies. This property provides a unique characteristic for each molecule. It provides a way to identify the molecule type. Since each type of molecule only absorbs light at certain frequencies, it provides a unique absorption spectral pattern, or fingerprint through the entire infrared light spectrum. In this manner, the more molecules of the same gas present in the sample, the more infrared light is absorbed at specific frequencies.

The FTIR system disclosed by Perez et al. is effective in identifying moisture contamination in a sample gas. The analysis provided by the Perez system permits a user in a facility to know quickly if a gas in a cylinder starts to stray from its acceptable concentration level. The Perez system alerts the user upon detecting a concentration level change in the gas.

The Perez system, however, only detects a concentration change in the moisture level present in the sample gas. As will be described, the present invention is much more advantageous than the Perez system, because it uses a computer network with a user interface to accurately control an FTIR module. The system of the present invention with its multiple software modules analyzes and determines the concentration level of a gas in a single cylinder, or the concentration levels of multiple gases present in a batch of gas cylinders. The present invention is sufficiently accurate to provide a certification to a user that the concentration level of a gas in the cylinder shipped to his facility is within one percent of that stated on a label posted on the cylinder. These and many more advantages of the present invention will be described in detail below.

SUMMARY OF THE INVENTION

To meet this and other needs, and in view of its purposes, the present invention provides a system for certifying to a user a concentration of gas in a cylinder. The system includes a gas cell configured to receive a sample gas from a cylinder, and an FTIR coupled to the gas cell for scanning the sample gas and forming a beam spectrum. A processor is coupled to the FTIR for calculating an intensity response of the sample gas based on the beam spectrum. A storage device is included for storing data points of a plot of intensity response of a known gas versus concentration levels. The processor is configured to interpolate between the stored data points of the plot to determine an interpolated data point corresponding to the intensity response of the sample gas, and provide to the user a concentration level of the sample gas based on the interpolated data point.

The processor is configured to execute an integration algorithm for determining an area of at least one region of the beam spectrum, and provide the determined area as the intensity response of the sample gas. The processor includes a curve fitting algorithm for finding data points of the intensity response of the known gas versus concentration levels, based on a plurality of scans performed by the FTIR on a corresponding plurality of cylinders each containing the known gas. The processor is configured to store the data points in the storage device as the plot of intensity response of the known gas versus concentration levels. The curve fitting algorithm depends on at least ten scans performed by the FTIR on a corresponding ten cylinders containing the known gas. The curve fitting algorithm uses at least one of a linear, quadratic, cubic or quartic orders of a polynomial equation.

In a further embodiment of the present invention, a gas cell of the system is configured to receive a sample gas from a cylinder, a standard gas from another cylinder and a zero gas from yet another cylinder. The FTIR is configured to scan the sample gas, the standard gas and the zero gas. The processor is configured to calculate an intensity response of the sample gas, an intensity response of the standard gas and an intensity response of the zero gas. The intensity response of the sample gas is Xn, the intensity response of the standard gas is Yn, and the intensity response of the zero gas is Zn. A resultant intensity response of the sample gas is based on the following equation:

$$Rn = \left(\frac{Ya}{Yn-Zn}\right)Xn - \left(\frac{Ya}{Yn-Zn}\right)Zn$$

where:

Xn is the sample results,

Yn is the standard results,

Ya is the actual results of the standard gas provided by the user,

Zn is the zero results, n is the number of the triad (3 per analysis), and

Rn is the resultant intensity response of the sample gas.

In another embodiment of the present invention, the gas cell is configured to receive a sample gas from a cylinder, a standard gas from another cylinder and a zero gas from yet another cylinder. The FTIR is configured to scan the sample gas, the standard gas and the zero gas. The processor is configured to calculate an intensity response of the sample gas, an intensity response of the standard gas and an intensity response of the zero gas. A resultant intensity response of the sample gas is calculated based on a sequence of first, second and third triads. The first triad includes a scan order of scanning first the zero gas, second the standard gas, and third the sample gas, and then computing a first correction. The second triad includes a scan order of scanning first the standard gas, second the zero gas, and third the sample gas, and then computing a second correction. The third triad includes a scan order of scanning first the standard gas, second the sample gas, and third the zero gas, and then computing a third correction. The resultant intensity response is based on the first, second and third corrections.

In another embodiment, a gas divider is disposed between the gas cell and the cylinder for diluting the concentration of the sample gas in the cylinder. When the sample gas in the cylinder has a concentration level greater than the concentration levels of the known gas stored in the storage device, then the gas divider is configured to dilute the sample gas before scanning.

The present invention includes a valve disposed at an output port of the gas cell. The valve is adaptively tunable to vent the gas from the output port. The processor includes a PID algorithm to tune the valve to vent the gas at a predetermined pressure level. The FTIR begins scanning the sample gas, after the PID algorithm tunes the valve to vent at the predetermined pressure level.

It is understood that the foregoing general description and the following detailed description are exemplary, but are not restrictive, of the invention.

BRIEF DESCRIPTION OF THE DRAWING

The invention is best understood from the following detailed description when read in connection with the accompanying drawing. Included in the drawing are the following figures:

FIG. 3 is an example of one menu displayed to a user for configuring portions of the system shown in FIGS. 1A-1C;

DETAILED DESCRIPTION OF THE INVENTION

Figure 1A:
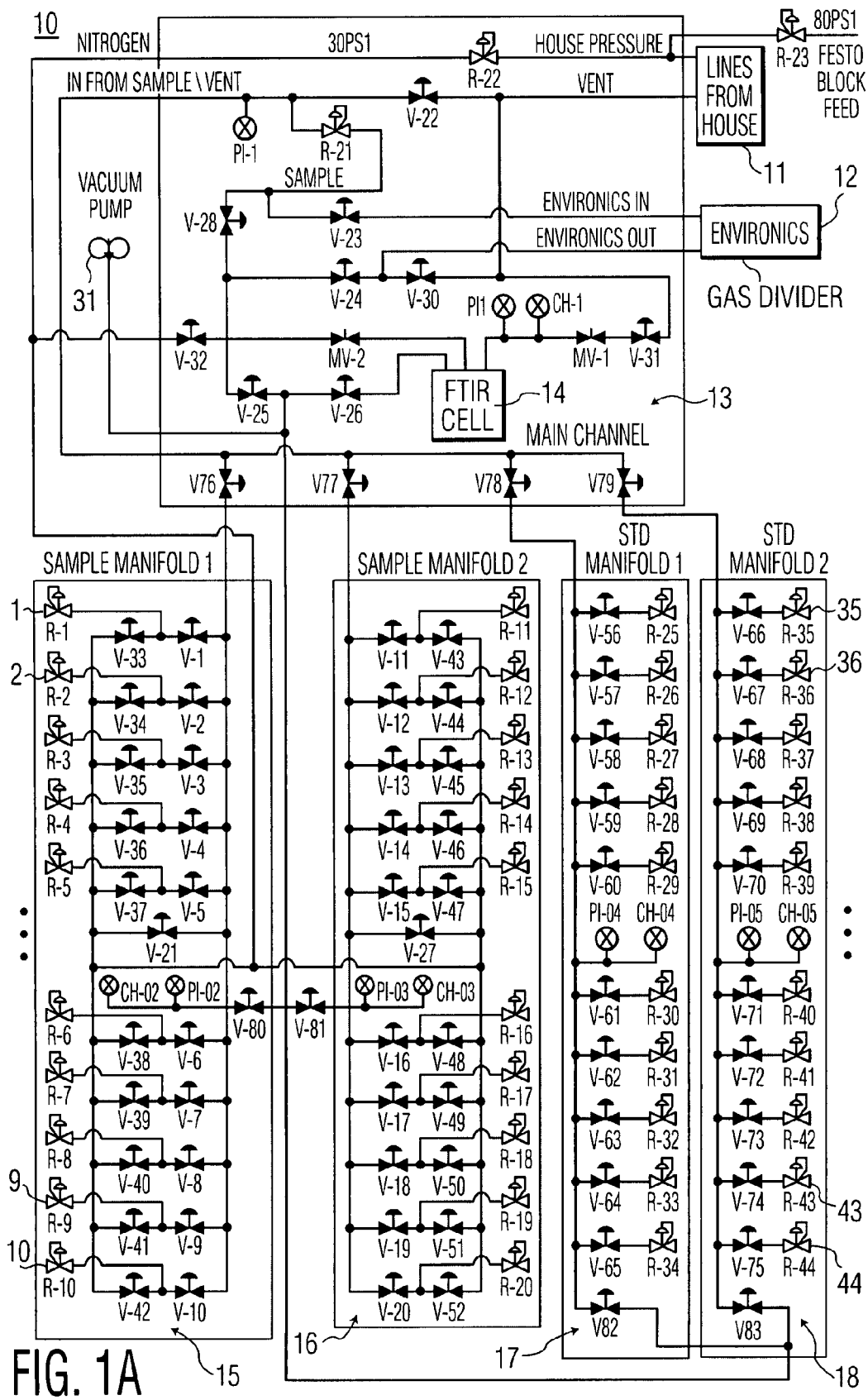
FIGS. 1A, 1B and 1C are functional diagrams showing a system for analyzing gas contained in a cylinder, in accordance with an embodiment of the present invention.
Figure 1B:
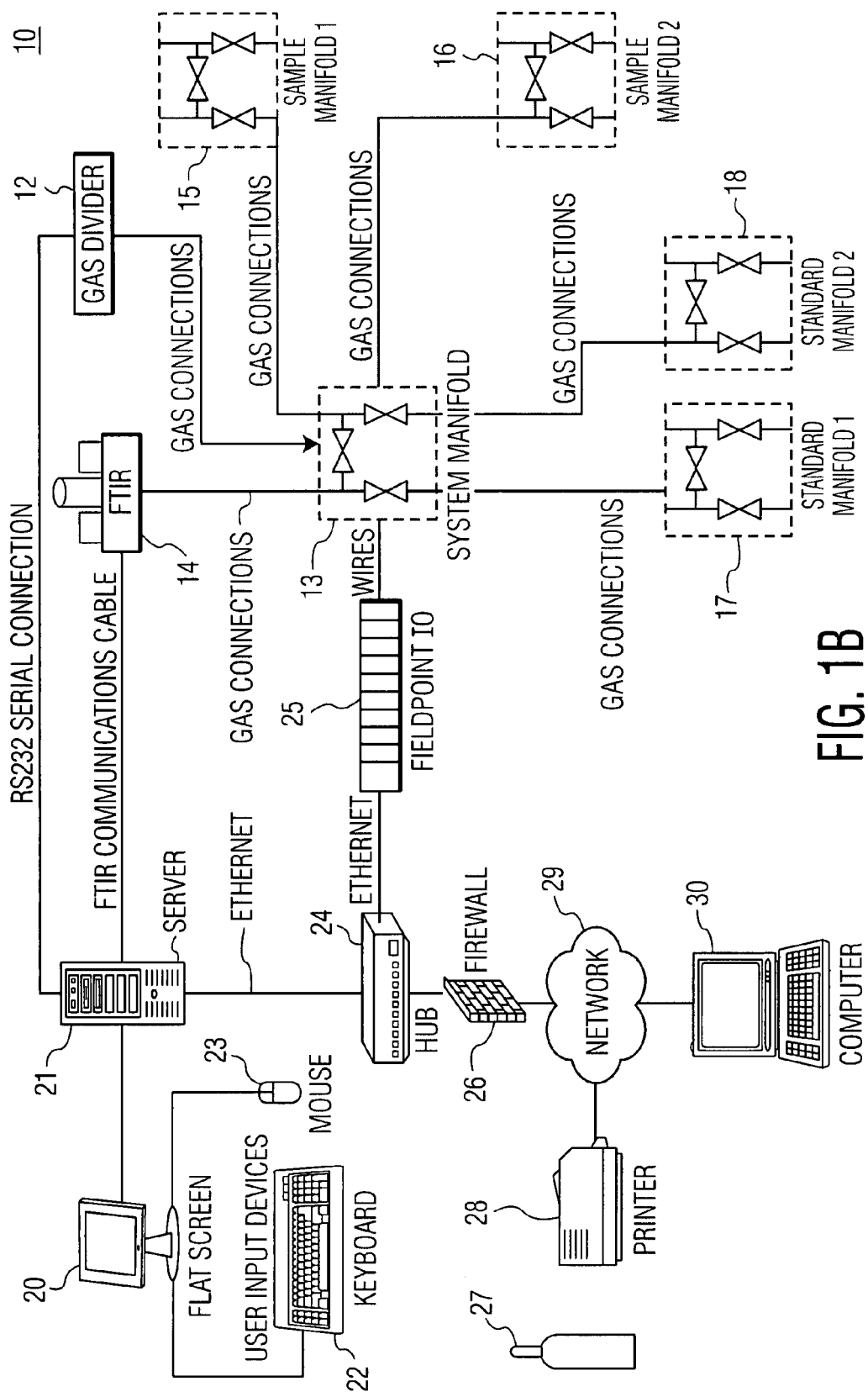
Figure 1C:
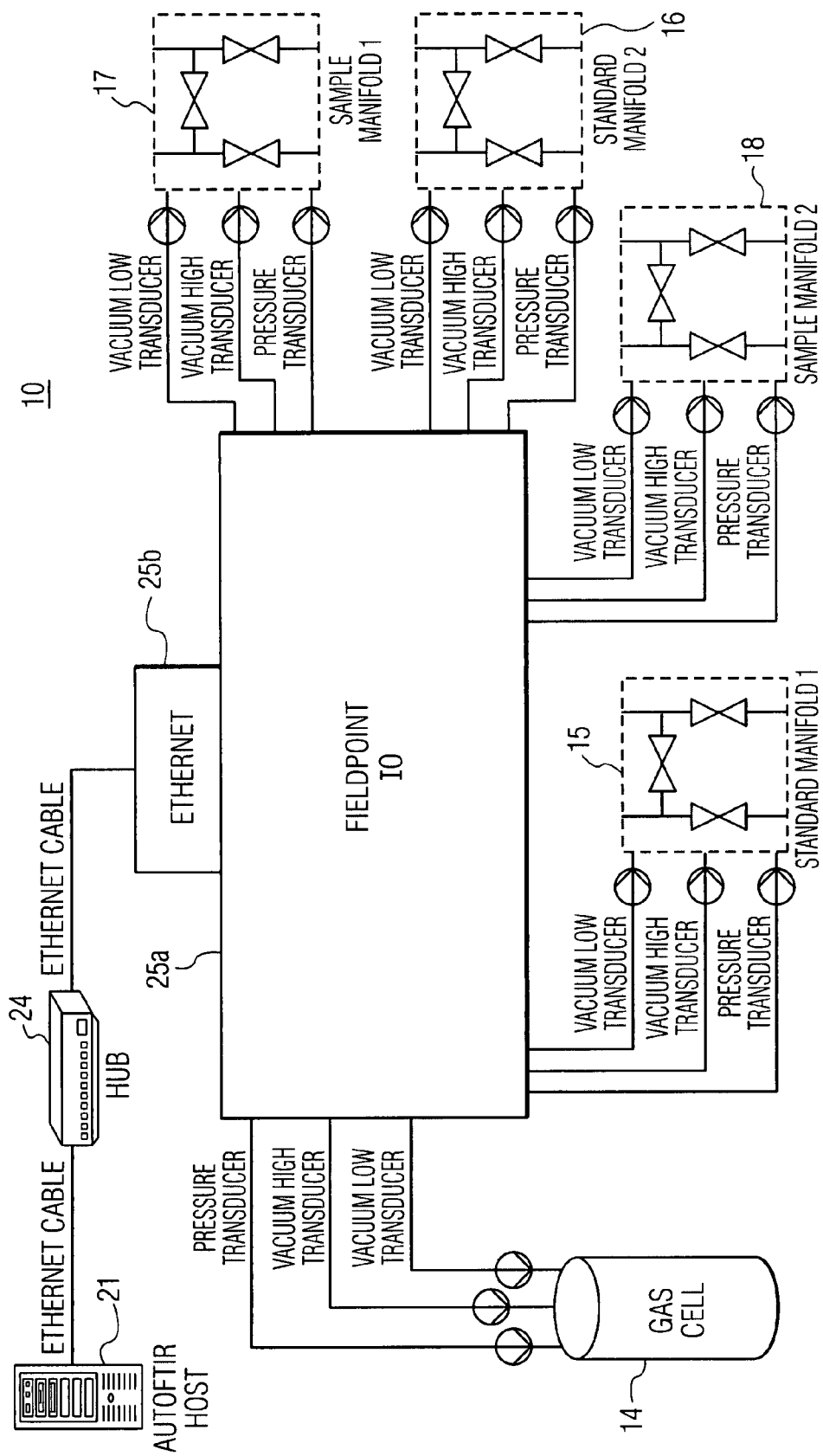

Referring to FIGS. 1A, 1B and 1C, there is shown a system for certifying concentrations of different gases in multiple cylinders, the system generally designated as 10. FIG. 1A shows the gas pipe connections among various valves and regulators in system 10, FIG. 1B shows communication connections between an FTIR module in system 10 and a computer network, and FIG. 1C shows multiple transducers providing pressure and vacuum readings to the computer network.

As shown in FIG. 1A, system 10 includes sample manifold 1, sample manifold 2, standard manifold 1, standard manifold 2 and a main cabinet, respectively designated as 15, 16, 17, 18, and 13. Sample manifold 1 provides connections from a sample gas cylinder (such as cylinder 27 shown in FIG. 1B). There may be as many as 10 different cylinders connected to input lines designated as 1, 2, etc., 9 and 10. Coupled to the sample gas cylinders are regulators R-1 to R-10 for lowering the pressure to approximately 40 PSIA into sample manifold 1. Similarly, sample manifold 2 may be connected to 10 additional sample gas cylinders (not shown) by way of regulators R-11 to R-20. Regulators R-11 to R-20 lower the pressure to approximately 40 PSIA into sample manifold 2. Standard manifold 2 provides coupling to 10 different standard gas cylinders (not shown) at input lines 35, 36, etc., 43 and 44. Regulators R-35 to R-44 lower the pressure from the standard gas cylinders to approximately 40 PSIA into standard manifold 2. In a similar manner, regulators R-25 to R-34 lower the standard cylinder pressure to approximately 40 PSIA into sample manifold 1. Accordingly, sample manifold 1 and sample manifold 2 provide as many as 20 different sample gas cylinders for feeding different sample gases into the FTIR module. Additionally, standard manifold 1 and standard manifold 2 provide as many as 20 different standard gas cylinders for feeding into the FTIR module.

A partial parts list is provided below for various elements in system 10.

located in main cabinet 13. Similarly, valves V-66 to V-75 provide automatic feeds to let standard gas from as many as 10 different standard gas cylinders, coupled to standard manifold 2, to flow toward valve V-79 located in main cabinet 13.

In operation, a sample gas may flow from sample manifold 1 through valve V-76, regulator R-21, valve V-28 and then through source variable valve MV 2, and finally into FTIR

TABLE 1

Partial Parts List for System 10

| Element | Manufacture | Part Number | Description |
|---|---|---|---|
| CH-1 | Teledyne | OBE-2002 | OBE Vacuum Transducer to read 1 mtorr to 760 torr for the Cell |
| CH-2 | Teledyne | OBE-2002 | OBE Vacuum Transducer to read 1 mtorr to 760 torr for Sample Manifold 1 |
| CH-3 | Teledyne | OBE-2002 | OBE Vacuum Transducer to read 1 mtorr to 760 torr for Sample Manifold 2 |
| CH-4 | Teledyne | OBE-2002 | OBE Vacuum Transducer to read 1 mtorr to 760 torr for Standard Manifold 1 |
| CH-5 | Teledyne | OBE-2002 | OBE Vacuum Transducer to read 1 mtorr to 760 torr for Standard Manifold 2 |
| 15 | Festo | 12P-10-MP-AR-W-11K + R | Festo Valve Block for valve control for Sample Manifold 1 |
| 16 | Festo | 12P-10-MP-AR-W-11K + R | Festo Valve Block for valve control for Sample Manifold 2 |
| 17, 18 | Festo | 10P-10-8C-MP-R-V-7CL + R | Festo Valve Block for valve control for Both Standard Manifolds |
| 13 | Festo | 12P-10-MP-AR-W-11K + R | Festo Valve Block for valve control for The Main Cabinet |
| MV-1 | MKS | 0148C-05000RM | MKS control valve Solenoid for Vent control |
| MV-2 | MKS | 0148C-10000RM | MKS control valve Solenoid for Fill control |
| PI-01 | Wika | | Pressure Transducer to read atmosphere to 50 psia for Main cabinet |
| PI-02 | Wika | | Pressure Transducer to read atmosphere to 50 psia for Sample Manifold 1 |
| PI-03 | Wika | | Pressure Transducer to read atmosphere to 50 psia for Sample Manifold 2 |
| PI-04 | Wika | | Pressure Transducer to read atmosphere to 50 psia for Standard Manifold 1 |
| PI-05 | Wika | | Pressure Transducer to read atmosphere to 50 psia for Standard Manifold 2 |
| R-01 to R-10 | Parker | IR4003SK4P01304B | Regulator to lower the cylinder pressure to Approximately 40 psia For Sample Manifold 1 |
| R-11 to R-20 | Parker | IR4003SK4P01304B | Regulator to lower the cylinder pressure to Approximately 40 psia For Sample Manifold 2 |
| R-21 | Parker | IR4003SK4P01304B | Sample Regulator to Internal manifold hold pressure to 20 torr |
| R-22 | Parker | IR4003SK4P01304B | Automatic Nitrogen Valve to hold pressure on system to 30 psia |
| R-23 | Airgas | Y11N145D | Nitrogen input to Festo outside cabinet to hold pressure to 80 psig |
| R-25 to R-34 | Parker | IR4003SK4P01304B | Regulator to lower the cylinder pressure to Approximately 40 psia For Standard Manifold 1 |
| R-35 to R-44 | Parker | IR4003SK4P01304B | Regulator to lower the cylinder pressure to Approximately 40 psia For Standard Manifold 2 |
| V-01 to V10 | Swagelok | 6LVV-DPFR4-P1-C | Automatic Sample valve to let sample gas into manifold for cylinder 1 to 10 on Sample Manifold 1 |
| V-11 to V20 | Swagelok | 6LVV-DPFR4-P1-C | Automatic Sample valve to let sample gas into manifold for cylinder 1 to 10 on Sample Manifold 2 |
| V-21 | Swagelok | 6LVV-DPFR4-P1-C | Automatic Valve to allow vacuuming of Main Manifold 1 |
| V-22 | Swagelok | 6LVV-DPFR4-P1-C | Automatic Valve to vent Main Manifold |
| V-23 | Swagelok | 6LVV-DPFR4-P1-C | Automatic Valve to allow gas out of manifold and into the Environics divider |
| V-24 | Swagelok | 6LVV-DPFR4-P1-C | Automatic Valve to allow divided gas from the Environics divider to the main manifold |
| V-25 | Swagelok | 6LVV-DPFR4-P1-C | Automatic Valve to allow the main manifold to be Vacuumed |
| V-26 | Swagelok | 4m4f-b6lj-ssp-c3 | Automatic ball valve to allow the cell to be Vacuumed |
| V-27 | Swagelok | 6LVV-DPFR4-P1-C | Automatic Valve to allow vacuuming of Main Manifold 2 |
| V-28 | Swagelok | 6LVV-DPFR4-P1-C | Automatic Valve to allow sample gas to get to the sample control valve to the Cell |
| V-30 | Swagelok | 6LVV-DPFR4-P1-C | Automatic Valve to allow the Environics to vent out to stabilize |
| V-31 | Swagelok | 6LVV-DPFR4-P1-C | Automatic Valve to allow the cell to Vent |
| V-32 | Swagelok | 6LVV-DPFR4-P1-C | Automatic Valve to allow Nitrogen to the Cell during off cycle trickle purge |
| V-33 to V-42 | Swagelok | 6LVV-DPFR4-P1-C | Automatic Valve for Nitrogen Purge to Cylinder 1 to 10 on sample manifold 1 |
| V-43 to V-52 | Swagelok | 6LVV-DPFR4-P1-C | Automatic Valve for Nitrogen Purge to Cylinder 1 to 10 on sample manifold 2 |
| V-56 to V65 | Swagelok | 6LVV-DPFR4-P1-C | Automatic valve to let standard gas into standard manifold 1 for cylinder 1 to 10 on Standard Manifold 1 |
| V-66 to V75 | Swagelok | 6LVV-DPFR4-P1-C | Automatic valve to let standard gas into standard manifold 1 for cylinder 1 to 10 on Standard Manifold 2 |
| V-76 | Swagelok | 6LVV-DPFR4-P1-C | Automatic Valve to enable Manifold 1 Sample |
| V-77 | Swagelok | 6LVV-DPFR4-P1-C | Automatic Valve to enable Manifold 2 Sample |
| V-78 | Swagelok | 6LVV-DPFR4-P1-C | Automatic Valve to enable Manifold 3 Standard |
| V-79 | Swagelok | 6LVV-DPFR4-P1-C | Automatic Valve to enable Manifold 4 Standard |
| V-80 | Swagelok | 6LVV-DPFR4-P1-C | Automatic Valve to allow Sample Manifold 1 to be Vacuumed |
| V-81 | Swagelok | 6LVV-DPFR4-P1-C | Automatic Valve to allow Sample Manifold 2 to be Vacuumed |
| V-82 | Swagelok | 6LVV-DPFR4-P1-C | Automatic Valve to allow Standard Manifold 1 to be Vacuumed |
| V-83 | Swagelok | 6LVV-DPFR4-P1-C | Automatic Valve to allow Standard Manifold 2 to be Vacuumed |

The manifolds include multiple valves to allow sample gas and/or standard gas from different cylinders to be fed into the FTIR module, designated as 14. Valves V-1 to V-10 let sample gas from sample manifold 1 toward valve V-76 located in main cabinet 13. Similarly, valves V-11 to V-20 let sample gas from sample manifold 2 toward valve V-77.

Furthermore, valves V-56 to V-65 are valves for letting standard gas from standard manifold 1 toward valve V-78 module 14 (also referred to herein as FTIR cell 14). Regulator R-21 holds the pressure from the output of sample manifold 1 at 20 torr. Source variable valve MV 2, which throttles the gas into gas cell 14 will be described in greater detail later. In a similar manner, sample gas from sample manifold 2 finds its way through valve V-77, regulator R-21, valve V-28, source variable valve MV2 and finally into FTIR cell 14. The gas flow from standard manifold 1 or standard manifold 2 into FTIR cell 14 is similar to the gas flow from sample manifold 1 or sample manifold 2, except that valve V-78 permits the gas to flow toward FTIR cell 14 from standard manifold 1 and valve V-79 permits the gas to flow from standard manifold 2 toward FTIR cell 14. The output flow of gas from FTIR cell 14 is provided by way of a vent variable valve, designated as MV1, which is a computer controlled valve. In addition, valve V-31 provides a path for venting the gas flowing out of MV1. As will be explained later, valve MV2 is also computer controlled.

As will be described in detail later, system 10 permits the concentration of a gas, before entering FTIR cell 14, to be reduced in concentration level by diluting the gas with an inert gas, such as nitrogen (N2). The concentration may also be diluted by using other gasses, such as oxygen (O2), helium (H2), etc. As shown in FIG. 1A, gas divider 12 (also shown as environics 12) provides a controlled process for diluting the gas from the cylinder. For example, valve V-23 allows a sample gas from sample manifold 1, 2 to be fed into gas divider 12. With valve V-24 open, the gas diluted by gas divider 12 is permitted to enter FTIR cell 14 by way of source variable valve MV 2. Valve V-30 permits gas divider 12 to vent its output gas for stabilization purposes.

The present invention advantageously eliminates manual control of the gas divider. An AutoFTIR system manifold is used to eliminate the manual action of connecting and disconnecting sample gases directly to the gas divider. The control of the gas divider is performed by the computer, as described later. The gas divider may be fully configured within an auto-batch process. A manual action on the display of the user is required only when configuring the batch for a divided gas sample. The divided gas may be stopped or started, without the user physically having to connect or disconnect sample gas cylinders. Gas library configurations are stored in the database and may be expanded by the user. The configuration handles mapping between the gas library, quant files (curves) and the divider gas library. This advantageously eliminates the tedious work otherwise required, when setting up the divider gas for any batch process.

The system of the present invention controls the gas divider to provide as little as 1% of a target gas to the FTIR module. The system may perform a single division or multiple divisions on a single target. As will be explained later, the system may divide a standard target gas to match the curve concentration levels being used in the FTIR analysis of a sample gas. After dividing the standard(s) for use in the creation of a response function, it becomes the response "curve" of the FTIR for the gas component of interest.

System 10 may be vacuumed by way of vacuum pump 31. Valve V-80 permits sample manifold 1 to be vacuumed and valve V-81 permits sample manifold 2 to be vacuumed. Similarly, valve V-82 permits standard manifold 1 to be vacuumed and valve V-83 permits standard manifold 2 to be vacuumed. The FTIR cell is permitted to be vacuumed by way of valve V-26. The main cabinet is permitted to be vacuumed by way of valve V-25.

As shown, nitrogen gas is provided to system 10 through pipelines from the house, generally designated as 11. The nitrogen gas is regulated by way of regulator R-22, which holds the pressure at 30 PSIA and regulator R-23, which holds the pressure outside the main cabinet at 80 PSIG.

Valves V-33 to V-42 are automatic valves for nitrogen purge to cylinders 1 to 10 on sample manifold 1. Similarly, valves V-43 to V-52 are automatic valves for nitrogen purge to cylinders 1 to 10 on sample manifold 2.

System 10 includes many transducers for sensing pressure at various points in the system. As shown in FIG. 1A and FIG. 1C, vacuum transducers, CH-1 to CH-5, provide pressure readings that vary from 1 mtorr to 760 torr, respectively, for FTIR cell 14, sample manifold 1, sample manifold 2, standard manifold 1 and standard manifold 2. FIG. 1C shows each of the vacuum transducers as two separate transducers, namely, a vacuum high transducer and a vacuum low transducer. Pressure transducers, PI-01 to PI-05, provide pressure readings that vary from one atmosphere to 50 PSIA, respectively, for main cabinet 13, sample manifold 1, sample manifold 2, standard manifold 1 and standard manifold 2.

Referring next to FIG. 1B, system 10 includes an Intranet network and an Internet network for controlling FTIR module 14 and controlling the openings and closings of the valves and regulators in main cabinet 13 (also referred to herein as system manifold 13), standard manifold 1 (15), standard manifold 2 (16), sample manifold 1 (17) and sample manifold 2 (18). Control of FTIR module 14 is provided from server/host/computer 21 by way of an FTIR communications cable. Control of gas divider 12 is provided from server 21 by way of an RS232 serial connection. Finally, Ethernet connections are provided between server 21 and hub 24, and between hub 24 and field point interface (IO) 25a, 25b. Server 21 may be accessed locally on the Intranet (LAN or WAN) by a user through keyboard 22, mouse 23 and flat screen display 20. Server 21 may also be accessed remotely on Internet 29 through protected firewall 26 by a remote user of computer 30 and printer 28. As shown in FIG. 1C, server/host/computer 21 communicates with field point IO 25a and Ethernet card 25b by way of an Ethernet cable. The field point IO converts analog signals provided from the multiple transducers into digital signals for transmission to server 21.

The server 21 may be considered to be a node on the Intranet/Internet and may be accessible anywhere with a VPN tunnel. In this manner, many nodes may be interconnected via the Intranet/Internet. This permits remote and local updates of any system operating as a node from other nodes operating elsewhere on the network. In addition, any node may be compared against another node for performance and reliability. In this manner, one node may be flagged as degraded in comparison to the operation of another node.

Figure 2:
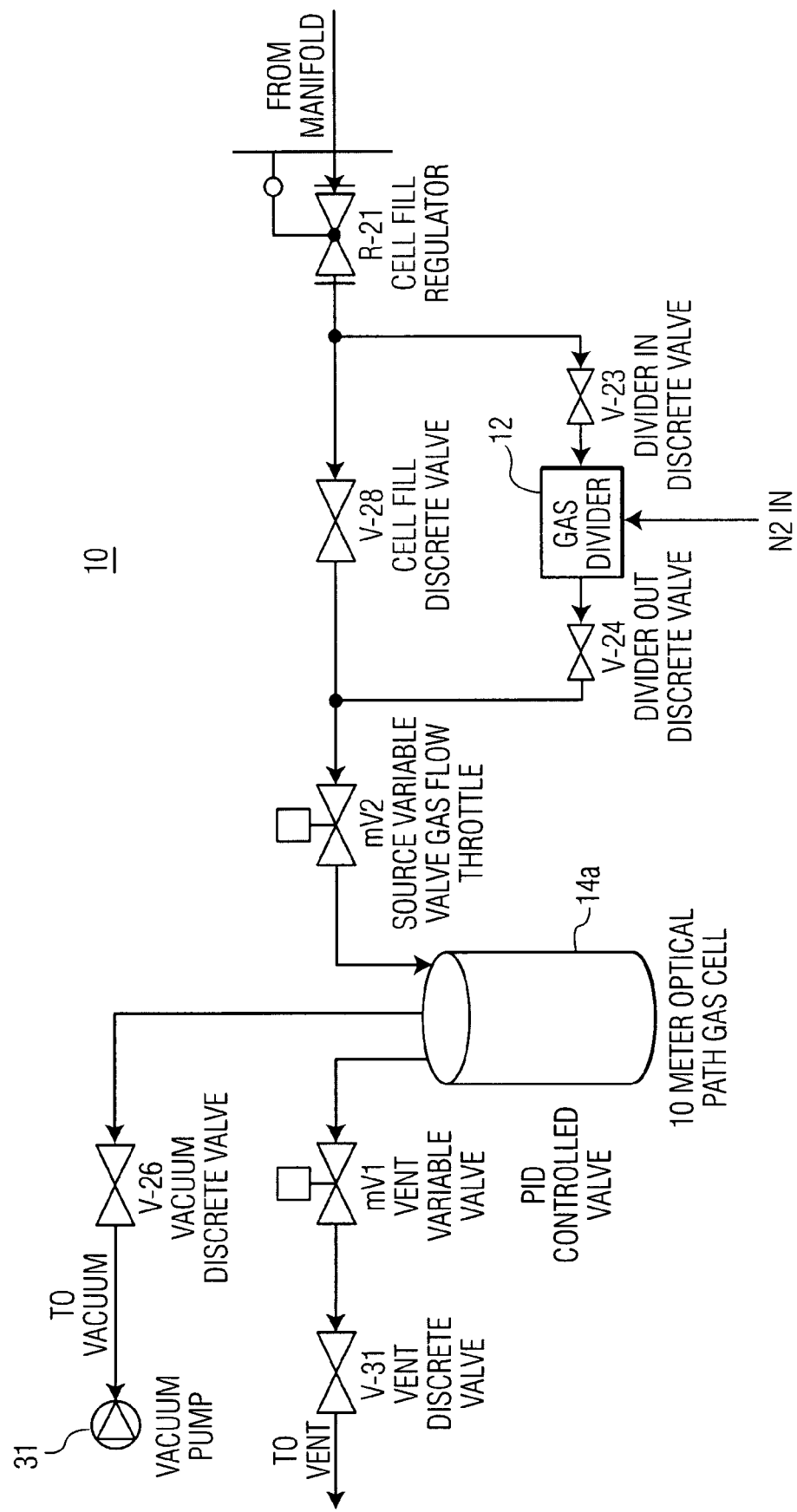
FIG. 2 is a functional block diagram showing greater detail of an input side and an output side of a gas cell included in the system of FIGS. 1A-1C.

Referring next to FIG. 2, the input side and output side of gas cell 14a of FTIR module 14 in system 10 are shown in greater detail. The input side includes regulator R-21 which regulates the pressure of the gas incoming from the four manifolds. Also included are a discrete on/off valve, V-28, and variable valve MV2, where the latter provides a throttle to the gas flowing into gas cell 14a. Disposed in parallel to V-28 and in between regulator R-21 and variable valve MV2 are gas divider 12 and discrete valves V-23, V-24. As shown, the gas incoming from the cylinders, whether diluted or undiluted by gas divider 12, is throttled by MV2 into gas cell 14a. The output from gas cell 14a is controlled by discrete valve V-31 and fine-tuned by variable valve MV1. Evacuation of the gas cell is provided by way of vacuum pump 31 and discrete valve V-26. Purging of the gas cell and stabilization of the gas cell prior to scanning will now be described.

A purge sequence of gas cell 14a may include the following steps:

1. Fill the gas cell to 800 torr with a single gas of interest (typically, may include a gas coming from a target cylinder, such as a sample gas, a standard gas, or a zero gas; may also include a gas coming from gas divider 12). During this step, discrete valve V-28 is wide open (value 65535 for a 16-bit analog channel on the IO).
2. Evacuate the gas cell to the vacuum pressure setting, which typically is 500 mTorr. The vacuum pressure is user configurable and may be modified.

3. Perform steps 1 and 2 for the number of times configured in the batch. For any particular gas of interest, the number of purge times is typically 2 purges.

The stabilization of the gas flowing into gas cell 14a is controlled by an algorithm executed by server/host/computer 21 (FIG. 1B). The stabilization algorithm may include the following steps:

1. After the purge sequence is performed, keep source variable valve MV2, fully open and pressurize the gas cell with the gas from the cylinder of interest.
2. At a predetermined user set pressure (typically set to 990 torr), set the source variable valve, MV2, to a stabilization cell pressure control setting. The stabilization cell pressure control setting, as shown in FIG. 3, may be viewed on display 20 provided to the user. As shown, the stabilization cell pressure control setting is unique to whether or not gas divider 12 (FIG. 2) is used to supply diluted gas to gas cell 14a.

The opening fractional value of MV2 is determined by the value of stabilization cell pressure control divided by 65535. Stabilizations using gas divider 12 utilize the control settings shown under Environics Control Settings. All other stabilizations, which do not use gas divider 12, utilize the control settings shown under Vent Control Settings. It will be appreciated that an amount out of 65535 determines the amount to which the pressure control valve is set, while pressurizing the gas cell before stabilization. As shown in FIG. 3, the pressurizing cell pressure control is initially set to a fully open position, which has a value of 65535 for a 16-bit analog channel.

3. From this point on, valve MV1 is precisely controlled by a PID algorithm executed by server/host/computer 21. The control of valve MV1 is described in greater detail later. The PID algorithm is fine-tuned by using parameters of Cell Stability Factor, Scan Pressure High, and Scan Pressure Low. The Cell Stability Factor is a predetermined value to determine when the gas cell is considered sufficiently stable, or when the gas cell has a standard deviation of pressure which is less than the Cell Stability Factor multiplied by the mean of the cell pressure. Scan Pressure High (torr) is the maximum pressure to which the gas cell is to be stabilized before a scan. The Scan Pressure Low (torr) is the minimum pressure to which the gas cell is to be stabilized before a scan.

It will be appreciated that, as shown in FIG. 3, the Scan Pressure High and the Scan Pressure Low are different when the gas divider is used to supply the gas cell and when the gas divider is not used. The computer examines the pressure readings from the Algorithm Switch Pressure every 100 iterations. The gas cell pressure reading buffers are cleared approximately every 10 seconds. The mean, the standard deviation, and the standard deviation of the mean are calculated.

4. The program determines whether the following condition is met:
If (standard deviation of the mean is<=Cell Stability Factor*mean) AND (mean<=Scan Pressure High) AND (mean>=Scan Pressure Low),
then the program commands the FTIR to begin scanning the gas. Typically, this condition is met within 30 seconds from the time the gas cell is beginning to fill with the gas of interest.
5. The Stabilization PID algorithm is continually applied until the scanning process is completed. The "Bleed-Through" setting in Batch Scan Type implies that the gas is continually permitted to flow through the gas cell during the entire scanning process. The Algorithm Switch Pressure (torr) is the pressure at which the stabilization algorithm takes control of ramping up the pressure in the gas cell.

It will be understood that the purge sequence and the stabilization sequence, described above, are repeated for each sample gas, each standard gas, and/or each zero gas. For example, if there are 3 gas sample cylinders, 3 gas standard cylinders and 1 zero gas cylinder in a batch, then the purge sequence and the stabilization sequence are repeated 7 times for each triad (a triad is explained later).

The PID algorithm compares a setpoint (SP) to a process variable (PV) to obtain an error (e), as follows:

$e = SP - PV$

Then the PID algorithm calculates the controller action, u(t), as follows:

$$u(t) = K_c \left( e + \frac{1}{T_i} \int_0^t e \, dt + T_d \frac{de}{dt} \right)$$

where $K_c$ is the controller gain.

If the error and the controller output have the same range (−100% to 100%), then controller gain is the reciprocal of proportional band. The $T_i$ is the integral time in minutes, also called the reset time, and $T_d$ is the derivative time in minutes, also called the rate time.

The following formula represents the proportional action:

$u_p(t) = K_c e$

The following formula represents the integral action:

$$u_i(t) = \frac{K_c}{T_i} \int_0^t e \, dt$$

The following formula represents the derivative action:

$$u_D(t) = K_c T_d \frac{de}{dt}$$

The following formula represents the error used in calculating proportional, integral, and derivative action, where $PV_f$ is a filtered process variable:

$e(k) = (SP - PV_f)$

Proportional action is the controller gain times the error, as shown in is the following formula:

$u_p(k) = (K_c * e(k))$

Trapezoidal integration may be used to avoid sharp changes in integral action, when there is a sudden change in the PV or SP. A nonlinear adjustment of the integral action may be used to counteract overshoot. The following formula represents the trapezoidal integration action:

$$u_i = \frac{K_c}{T_i} \sum_{i=1}^{k} \left[ \frac{e(i) + e(i-1)}{2} \right] \Delta t$$

Because of abrupt changes in the SP, derivative action may be applied to only the PV, not to the error (e), to avoid derivative kick. The following formula represents the partial derivative action:

$$u_D(k) = -K_C \frac{T_d}{\Delta t}(PV_f(k) - PV_f(k-1))$$

The controller output of the PID algorithm when controlling variable valve MV1 is the summation of the proportional, integral, and derivative action, as shown in the following formula:

$$u(k) = u_p(k) + u_I(k) + u_D(k)$$

Figure 4:
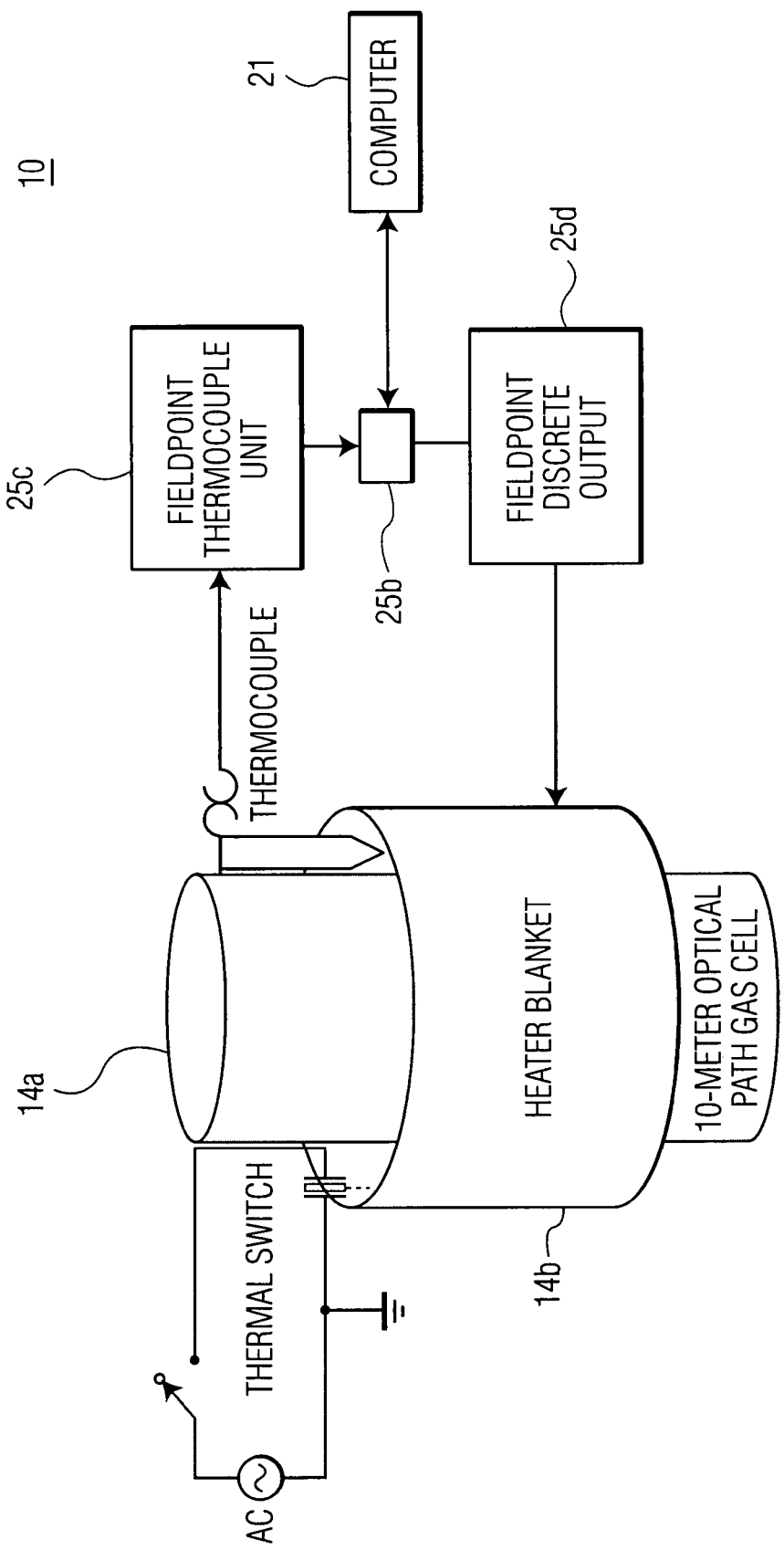
FIG. 4 is a block diagram of a heater blanket that envelops the gas cell and is controlled by a computer of the system shown in FIGS. 1A-1C.

In addition to the present invention having a PID control loop for precisely controlling the venting of a gas from gas cell 14a, the present invention also provides a PID control loop for stabilizing the temperature of gas cell 14a. As shown in FIG. 4, system 10 includes heater blanket 14b for surrounding gas cell 14a. A thermocouple and a thermal switch are also included adjacent to gas cell 14a. Although not shown, both are actually completely blanketed by heater blanket 14b. The heater blanket tightly wraps the gas cell for further stabilizing the gas cell environment.

The thermal switch, shown in FIG. 4, provides protection to gas cell 14a against the possibility of overheating the gas cell. As such, the thermal switch is opened when the temperature exceeds a predetermined limit. The thermocouple provides the temperature reading at the gas cell to fieldpoint thermocouple unit 25c (automation direct fieldpoint IO thermal analog input unit). The automation direct IO then relays the temperature reading, through Ethernet card 25b (using modbus IP protocol) to computer 21. Another PID control algorithm, executed by computer 21, is used to control the heater blanket. The PID control algorithm provides a control signal to fieldpoint discrete output 25d by way of Ethernet card 25b. The signal is converted into an analog signal for controlling the temperature of the heater blanket.

The PID algorithm controls the heater blanket using pulse width modulation (PWM) control. The heater has two states, on and off. The PWM control turns on the heater (no throttling) for a specific duration. The PID loop receives the temperature input from the thermocouple and makes a determination when to next turn on the heater. The rate of change in the PID PWM control is determined by how many times the heater is turned on and off. In this manner, the present invention precisely controls the temperature environment of the gas cell.

Figure 5A:
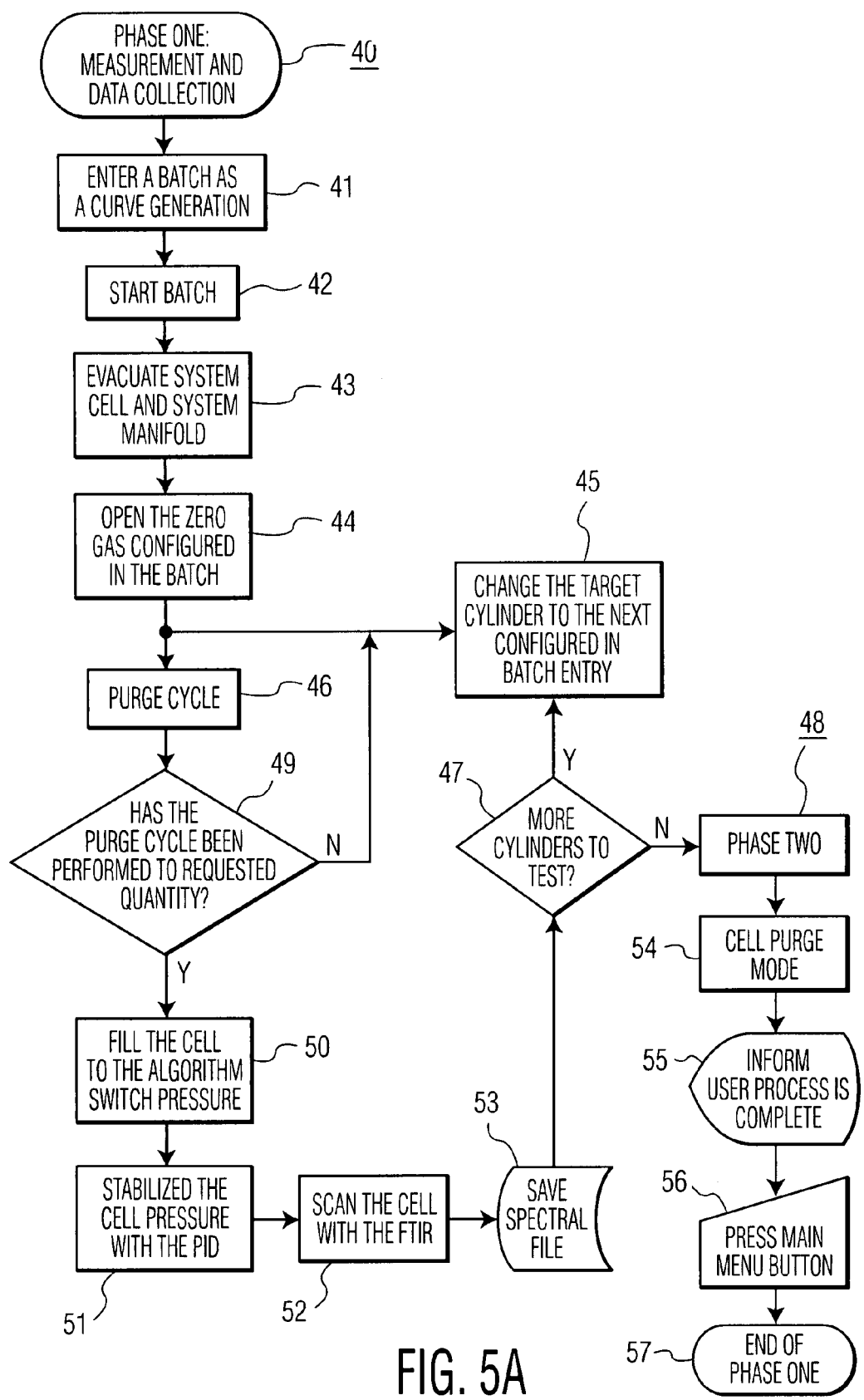
FIG. 5A is a flow diagram showing a measurement and data collection method of the present invention, in accordance with an embodiment of the present invention.
Figure 5B:
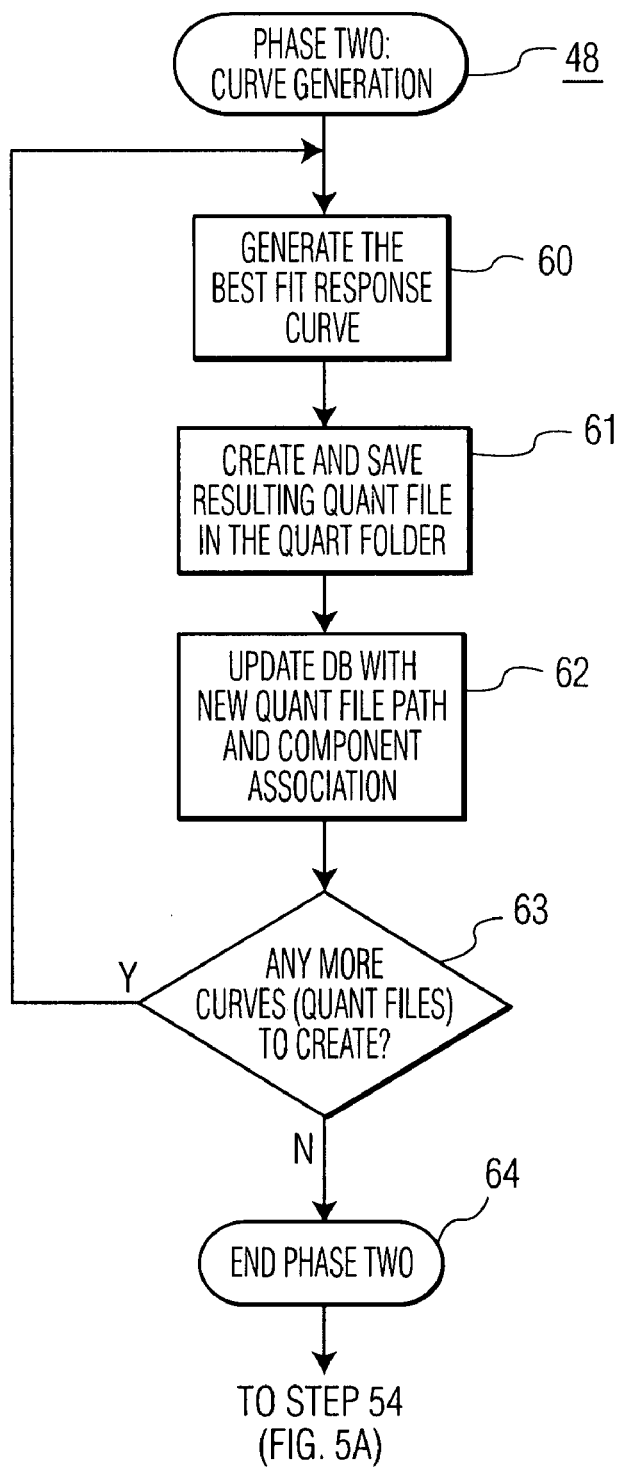
FIG. 5B is a flow diagram showing a curve generation method of the present invention, in accordance with an embodiment of the present invention.

The manner in which the present invention builds a database of response curves (look up tables), against which the concentration level of a sample gas cylinder may be compared, will now be described by reference to FIGS. 5A, 5B, 5C and 5D. Referring first to FIGS. 5A and 5B, there is shown a method that includes a measurement and data collection process (referred to as phase 1) and a curve generation process (referred to as phase 2), respectively designated as 40 and 48. The phase 1 process includes the following steps:

Steps 41 and 42 allow the user to control a batch of several gas cylinders for purpose of curve generation. It will be appreciated that in order to generate a typical curve, as many as 10 different gas cylinders may be required in the batch. Each of these 10 different gas cylinders may include a known concentration of a specific gas (for example, 10 CO gas cylinders having concentration levels of 50 ppm, 70 ppm, 100 ppm, 150 ppm, etc.). Some, or all but one point generated on the curve may be based on a divided gas and does not have to be a pure sample.

The method begins with the first cylinder in the batch (step 42). The gas cell and the appropriate manifolds are evacuated in step 43. System 10 is then purged by using a zero gas (for example nitrogen) for the entire batch (step 44). The method uses a zero gas to purge the system for a predetermined number of cycles. A typical number for purge cycles is 2 times. After completing the number of purge cycles (steps 46 and 49), the method enters step 50. The gas cell is filled, by way of source variable valve MV2, to the predetermined Algorithm Switch Pressure. Such switch pressure may be 990 torr, as displayed on the menu shown in FIG. 3, for example.

Figure 5C:
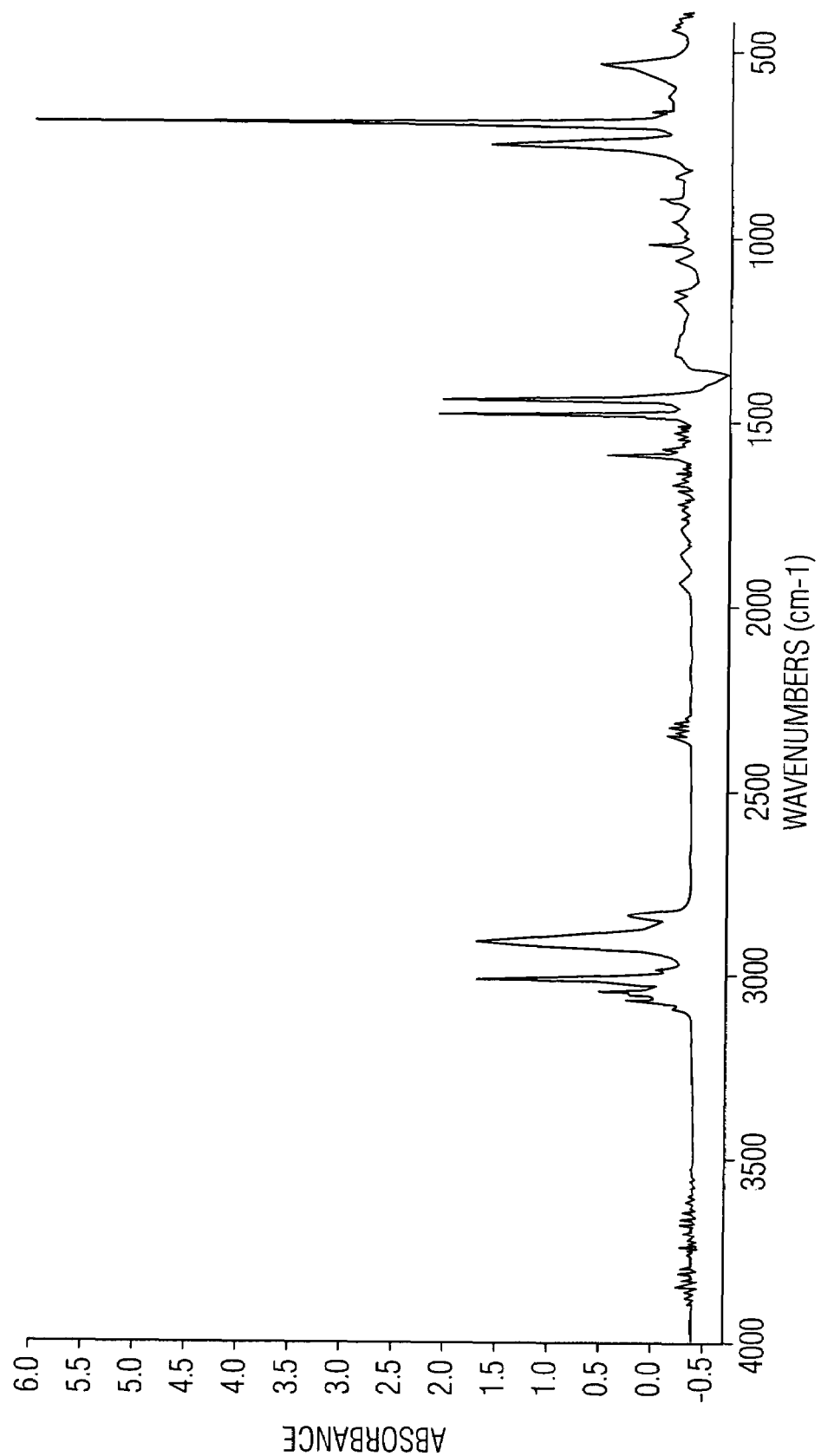
FIG. 5C is an exemplary plot of absorbance versus wave numbers.

After filling the gas cell to the predetermined switch pressure, step 51 begins stabilizing the gas cell pressure by using the PID stabilization algorithm, described earlier. After the pressure is stabilized, step 52 begins scanning the gas cell. The FTIR produces an interferogram, which may be a plot of absorbance versus wave numbers (or a list of collected values stored in a look-up-table). An exemplary hypothetical plot of absorbance versus wave numbers is shown in FIG. 5C. As shown, the hypothetical gas is absorbed by the infrared light at approximately 2950 wavenumber, 3100 wavenumber, 1520 wavenumber, 1540 wavenumber, etc. The method in step 53 saves the spectral plot (a set of data points) in a storage file.

If more gas cylinders in the batch are to be scanned, as determined by decision box 47, the method loops back to step 45 and automatically changes the target cylinder to the next configured cylinder in the batch as first entered by the user. The purge cycle is repeated for the predetermined number of times, the gas cell is filled and stabilized again to the desired pressure, and another scan is taken of the target gas.

Another spectral plot is obtained in step 53. Since the presently scanned gas is the same gas (for example CO) but includes a different concentration level than the previously scanned gas, the interferogram presently generated by the FTIR is likely to appear similar to the previously generated interferogram. However, depending on the concentration level, the peaks and the valleys of the two interferograms may vary in amplitude.

When all the cylinders have been scanned, as determined by decision box 47, the method enters the phase 2 process, designated generally as 48, as shown in FIG. 5B. Still referring to FIG. 5A, after completing the phase 2 process, the gas cell is purged in step 54, and the user is informed in step 55 that the process has been completed. The user may then press a menu button on his display (step 56) to end the phase 1 and phase 2 processes (step 57).

Referring now to the phase 2 process shown in FIG. 5B, the method in step 60 generates a best fit response curve to the multiple interferograms that have been individually generated and stored during the phase 1 process. While the phase 1 process generates the automated data collection of the spectra, the phase 2 process generates the automatic creation of the actual quantification of concentration levels (ppm) per specified response values (curve fitting).

Figure 5D:
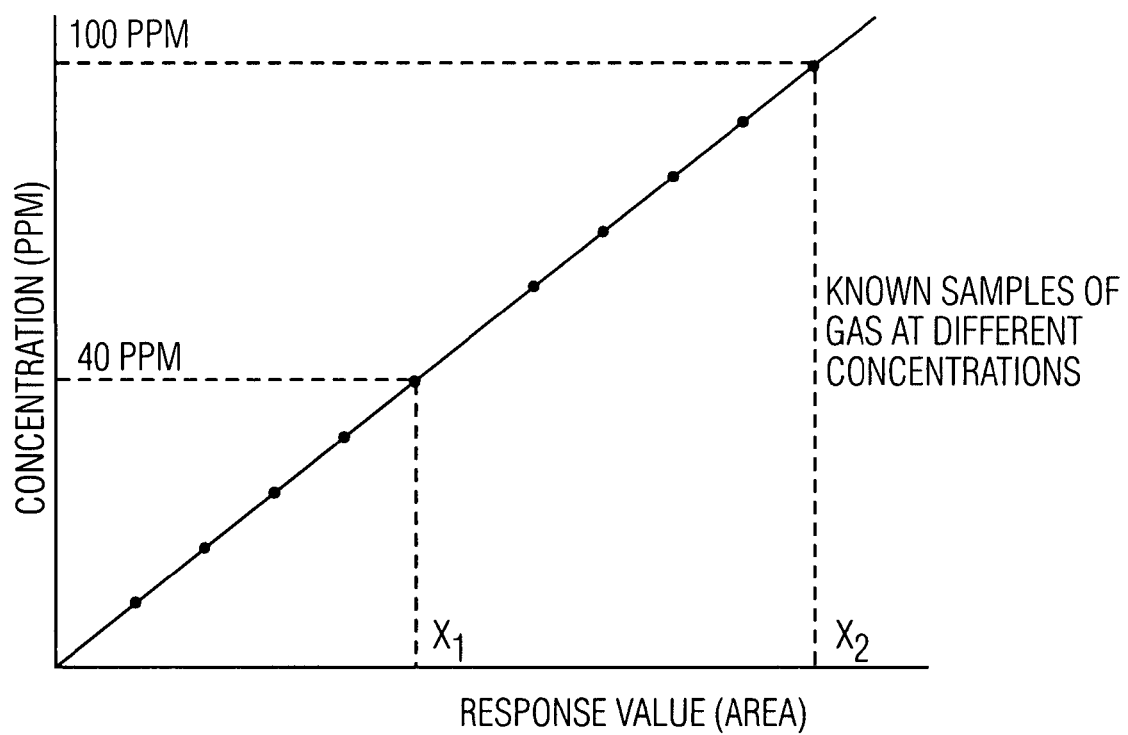
FIG. 5D is a linear curve of concentration versus response value of a known gas which has been sampled at different concentration levels, in accordance with an embodiment of the present invention.

In one exemplary method, the best fit response curve may be generated by finding the area under the spectral curve shown in FIG. 5C. The method need not calculate the area under the entire curve, but needs only to find the area at certain regions under the curve. For example, in the interferogram shown in FIG. 5C, the method may calculate the area between wave numbers 2800 and 3100 and/or the area between wave numbers 1400 to 1600, and/or the area between wave numbers 500 to 800. The total area under the desired regions under the spectral curve provides the response value (area) of a specific gas at a specific known concentration level (ppm). For example, one target cylinder may have a known concentration of 40 ppm CO. After being scanned, the area calculated under the desired regions of the resulting interferogram may result in an area of $x_1$, as shown in FIG. 5D. As another example, shown in FIG. 5D, the same gas contained in a different target cylinder may have a known concentration of 100 ppm and result in a response value of an area of $x_2$.

Other methods may also be used for generating the best fit response curve. Such methods may include, but not be limited to, spectral region, peak height, and peak width methods.

Background and baseline effects may also be subtracted from the regions of the spectral file (interferogram), before applying the above described response generating algorithm (for example, finding the area under a spectral curve). A background test may be taken before the batch. The computer may perform a regression algorithm (may be linear regression) to find the baseline effects. The baseline effects may then be subtracted from the regions of the spectral file (interferogram).

As many as 10 different gas cylinders of different known concentrations of one specific gas may be required to complete the entire curve shown in FIG. 5D, for example. After the response values (area) of these 10 different gas cylinders have been calculated, a best fit function is estimated to generate the curve shown in FIG. 5D. It will be appreciated that the curve shown is a straight line, but a straight line is not always the best fit. A general function which expresses the best fit response curve is as follows:

$$f(x) = a_0 + a_1 \cdot x + a_2 \cdot x^2 + \ldots + a_n \cdot x^n$$

where
x is the function input,
n is the order of the curve fit,
$a_0$=constant coefficient,
$a_1$=first order coefficient,
$a_2$=second order coefficient, and
$a_n$=nth order coefficient.

Many spectral curves are needed to generate the above curve coefficients. The present invention stores all the known standard spectral files in a directory in the server database. These spectral files may be read, when generating these curve coefficients. After completion of a batch test, the computer program prompts the user to enter the actual concentration levels. The computer program applies one of many possible curve fitting methods to minimize the error in the curve fit when generating the curve coefficients. The various curve fitting methods may include classical least squares, partial least squares, Beers law, etc.

After having obtained a curve of concentration versus response value (for example, CO concentration levels in ppm versus area), system 10 of the present invention is ready to certify a corresponding target gas in a cylinder (for example CO gas).

It will be appreciated that system 10 is sufficiently accurate to provide a close agreement (less than one percent error) between a calculated response curve based on FTIR scans and actual known responses based on previously stored spectral files. In one such comparison, the difference between the actual concentration values and the calculated concentration values were less than 0.026 ppm.

Returning to FIG. 5B, step 61 of the method creates and saves a quantitative file in a folder of the system database. One such file may be a look-up-table of concentration in ppm versus response value in area for a specific gas (for example CO). The database may also be updated in step 62. If no more quantitative files are to be created, as determined by decision box 63, phase 2 ends in step 64 and the method branches back to step 54. If decision box 63 determines that more quantitative files are to be created and stored in the database, the method loops back to the beginning of the curve generation phase, as shown in FIG. 5B.

As another operational mode, system 10 of the present invention is effective in certifying the concentration level of a sample gas cylinder (a target cylinder). In order to improve the quality of the certification, the present invention requires that for each sample gas cylinder, a standard gas cylinder (a standard of known concentration) and a zero gas cylinder (an inert gas, typically nitrogen) also be used. Accordingly, the present invention scans a sample gas cylinder with a standard gas cylinder and a zero gas cylinder. This is referred to herein as a "triad" and includes a first triad, a second triad and a third triad. The difference in the three triads is the order of testing of the cylinders.

For example:

Triad 1 has the following test order: first, the zero gas; next, all the standards; and last, all the samples.

Triad 2 has the following test order: first, all the standards; next, the zero gas; and last, all the samples.

Triad 3 has the following test order: first, all the standards; next, all the samples; and last, the zero gas.

Figure 6:
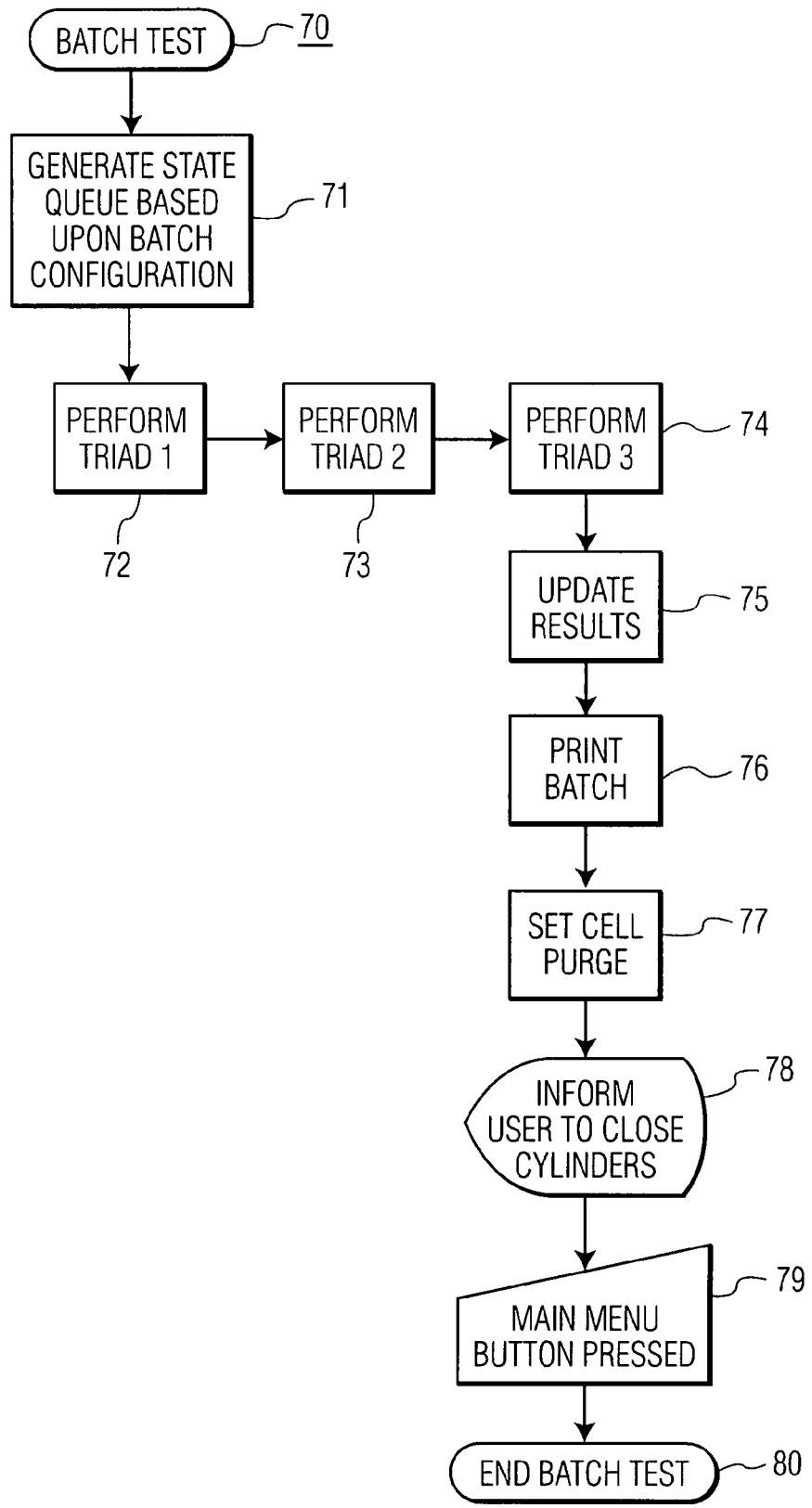
FIG. 6 is a flow diagram showing a batch test, in accordance with an embodiment of the present invention.

Referring now to FIG. 6, a method for testing a batch of cylinders is shown generally as method 70. As shown, step 71 configures the batch test in the appropriate order. For example, triad 1 is tested first in step 72. Triad 2 is tested second in step 73. Lastly, triad 3 is tested in step 74. After all three triads have been tested, only then is system 10 prepared to certify the sample gas cylinder. As an example, assuming that only three cylinders are part of a batch, where one cylinder is a sample gas cylinder, the second cylinder is a standard gas cylinder and the third cylinder is a zero gas cylinder. A possible sequence of testing the cylinders includes first testing triad 1, which first scans the zero cylinder, the standard cylinder is scanned second and the sample cylinder is scanned last. The next sequence is shown as step 73, the tests are repeated in a triad 2 order, namely first the standard gas cylinder is tested, next the zero gas cylinder is tested and, finally, the sample gas cylinder is tested. Last in sequence is step 74, which performs a triad 3. This includes the following order: first, the standard cylinder is tested; next, the sample gas cylinder is tested; and finally the zero gas cylinder is tested. Consequently, in certifying a single sample gas cylinder, system 10 performs 9 different sequences of tests.

Completing the description of FIG. 6, the method updates the results in step 75 and prints results of the batch test in step 76. The gas cell is purged in step 77 and the user is informed to close the cylinders in step 78. The batch test is concluded upon pressing the main menu button on the user's display (steps 79 and 80).

The following is a description of the calculations performed by the system for each component gas of interest. There may be several component gases of interest within a sample. For each one component gas, a standard gas concentration for that particular component is required. These standard gas concentrations may be within one or multiple standard gas cylinders.

The following are the triad calculations:

Sample results=Xn

Standard Results=Yn

Standard Actual (actual concentration of the gas of interest, provided as input by the user)=Ya Zero Results=Zn The n is the number of the triad (3 total per analysis).
Scale Factor Correction:

$$Fn = Ya/(Yn - Zn)$$

Sample Zero Correction:

$$Cn = Xn - Zn$$

Single Undiluted Sample Triad Result:

$$Rn = Fn * Cn$$

Average Sample Results:

$$\overline{R} = \sum_{n=1}^{3} Rn/3$$

Error Analysis:
Sample Standard Deviation:

$$StdDev = \frac{\sum_{n=1}^{3} (Rn - \overline{R})^{1/2}}{3}$$

Sample Standard Deviation of Mean (aka Standard Error of Mean):

$$SSDM = Std\ Dev/(n)^{1/2}$$

Results of a Sample:

$$\overline{R} \pm SSDM$$

The cylinder passes certification, if $$SSDM \leq \frac{\overline{R}}{100}$$

Accuracy is established by the present invention in the application of the sample response to the curve, the results of which are the Sample Results Xn, Yn, and Zn. This application is also referred to as the curve correction.

The quantification of accuracy is more difficult. In the curve generation process, accuracy is apparent by the amount of scatter in the data. The calculated error due to scatter in the curve data, coupled with the agreement of the curve with the validation point, allows the user to quantify the accuracy of the process. Also, the present invention mines various types of data to ensure accuracy Such type of information includes the concentrations added to all the cylinders, and the agreement of test results of system 10 with the concentration targets. In addition, the present invention mines for the scatter in the data between desired concentration of a sample gas and a measured concentration of the sample gas. All this data adds to the confidence of the system's output results.

In a case where the target sample must be diluted first before scanning, because the target sample has a concentration which is larger than the curve limits, the present invention performs the following correction, in addition to all of the above described corrections:

For each triad n, the curve is corrected as follows:

Start Concentration = Sn

End Concentration = En $$Xn = Cn * Sn/En$$

Figure 7:
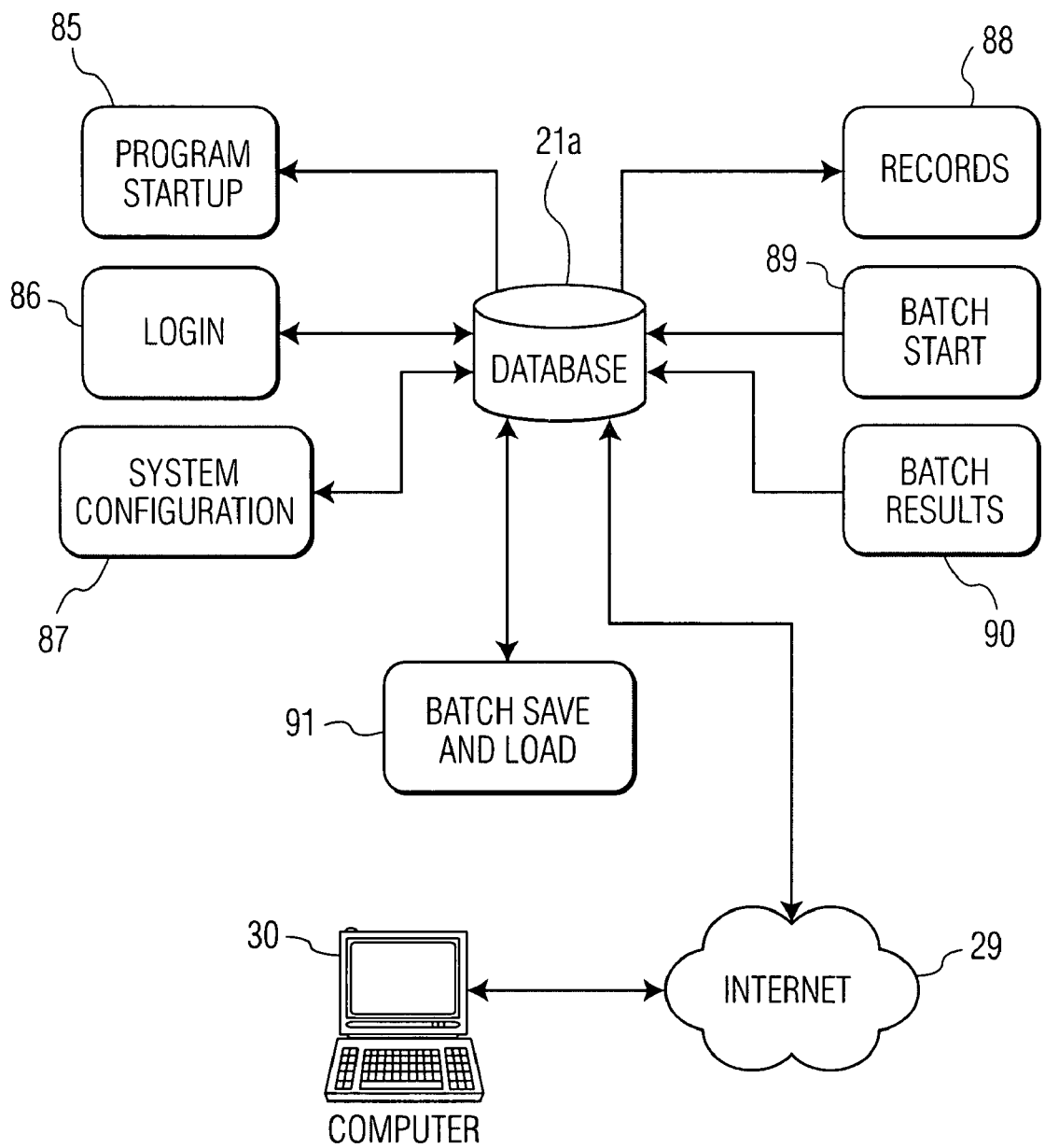
FIG. 7 is a block diagram showing an interface between the user and different application programs executed by the computer of the system shown in FIGS. 1A-1C, in accordance with an embodiment of the present invention.

The interface between the user and system 10 is shown functionally in FIG. 7. As shown, a user may interface with database 21a of host server 21 (shown in FIG. 1B) by way of program startup 85, login procedure 86, system configuration 87, system records 88, batch start 89, batch results 90, and batch save and load 91. The login procedure 86 handles login for the user on a screen and allows the user to login with a secure user ID and password. A user may only login as himself. This facilitates tracking the user's productivity and work pattern (may be generated as part of user metrics). The user ID and password may also be used by the system to deny access by lower level users to certain reports. Program startup 85 allows the user to initialize and display the main menu, and to navigate to different parts of the application.

The system provides a graphical user interface (GUI) which supports the functionality of an automatic batch test by the system (AutoBatch). This provides user interactions, such as entering a batch test, interacting with the AutoFTIR program to start a test, and informing the user of possible problems. The AutoBatch also provides the user runtime information in a PI&D format. In this manner, the user may readily understand the operation of the system. The GUI structure also provides the user with a PI&D format for intuitive manual control over the system in performing various operations (including operations not part of the AutoBatch function. The following is provided to the user:

a. A subtab, which displays only the currently necessary information.
b. A subtab for the indication of auto-batch current state, through named Booleans.
c. A subtab of manual mode options, such as
   Hardware control macros, which perform routine hardware manipulations.
   Manual variable Valve Control sliders.
   Individual discrete valve control, through the same valve state indicators in auto-batch.
   A list of selectable manual scan ranges of components configured in the database.
d. A dialog subtab for text indication to the user. Without this, a problem required an abort, or an end of a run. The same dialog subtab also has option buttons, for required user actions.
e. A subtab for the display of the control graph, with statistics output, to indicate to the user how well the cell pressure and temperature is controlled during crucial periods.
f. A batch results window, which displays current batch results of a selected cylinder, configured within the batch.
g. A virtual control panel, which displays the complete valve states to a user at a glance.
   Contains a virtual representation of the piping paths.
   Contains a representation of all the discrete control valves.
   Contains a representation of both the variable control valves.
   Contains a representation of the cell pressure, both numerically, and as a graphical cell, being filled.
   Contains a representations of the FTIR and a working representation of the divider, with measured and desired values.
   Contains a scalable representations of the standard and sample manifolds. Scaleable to any reasonable multiple of 10 cylinders, per manifold.
   Indications of current pressure readings, from 0 mtorr, to 2586 torr (50 psi), on all manifolds and the cell.
   A cell temperature indication.

An abort button, for manually aborting an auto-batch test.

h. Programmatically executes the EPA testing procedure, or the curve generation process. All without human intervention (once configured).

i. Evaluates pressure conditions, and provides timer to detect physical problems with the gas supply.

j. Precisely controls the gas supply to the cell, and detects physical problems with PID-feedback control.

k. Autonomously controls the Omnic interface to the FTIR.

l. Automatically stores results into an ODBC relational database.

m. Saves all spectral files with the current time, date and work order numbers, cylinder numbers, and actual divider division concentration (for curve generation).

n. Autonomously controls the divider, once the batch is configured.

o. Can perform any configured number of purges configured, as well as any level of vacuum, on a per-sample basis.

p. Autonomously update the result details to a website, after the Batch test is complete. Saves hours of updating a day.

Still referring to FIG. 7, the system configuration 87 permits the user to configure various parameters, which changes the behavior of the system. For example, the user may configure the divider module, the FTIR interface programs, timer settings, IP addresses, standard lines, components, quantitative files, etc. The batch start 89 permits the user to begin the batch test. The batch results 90 permits the user to request the results of the batch test for viewing on the display. Results of the batch test are always saved to database 21a using the batch save and load 91. In this manner, the batch setup parameters may always be recalled by the user. Records of the batch test may be provided to an external user by way of records 88, which also allows the user to view the records. The user may also view a summary of each work order on the screen. A detailed view of a work order provides the user with a cylinder-centric view which may also be printed. The reports may also include, for each work order, the component results, the mean and the standard deviation of the mean (final error in the analysis).

The system configuration provides the user an easy ability to configure the system for a wide variety of gas testing scenarios. Because the GUI and the computer database are functionally integrated, the present invention permits the user, after being granted permission to access the system, to configure every part of the system, save the configuration parameters into the database, and recall configuration parameters during different execution cycles of the program. Without this, the user would have to manually reconfigure the system during every execution cycle. The following functions are provided by the system by way of the configuration module:

a. User Management
Add Users
Delete Users
Edit Users
View users and their passwords.
b. Standards
View all standards configured.
Edit any Standard Configured
Add a new standard to an available standard manifold line.
Delete non-existent standard to make a particular standard line available.
c. Quant Setup Maps an existing component range to a quantification (quant) file, to be used in the analysis by Omnic.
Add a new quant file mapping.
Delete an existing quant file mapping.
View all quant file maps.
Check for the existence of all qualt files previously mapped.
Important, since the user may move or delete an existing quant file, without modifying the quant file to component range map.
d. Ranges and Components
Can add a component concentration range as a core component (available for use as a quantifiable component), or impurity (only available for qualification of an impurity; no corrections to the final result, nor requiring a standard for analysis).
Can delete an existing component range. Note, this will also remove the component range from the quant file configuration table, as well as any standards configured to use the deleted component range.
Can edit any of the properties of the component range.
e. Pressures
Vacuum default setting for batch builder.
Purge Pressure default setting.
Number of Purges defaults setting.
Cell Purge Vent Control setting. The precise value which to open the cell vent control valve, while trickle purging the cell.
Cell Purge Source Control setting. The precise value to set the cell source control valve, while trickle purging the cell.
f. Heater Control
Dial control with digital numerical setting for the target cell temperature, in degrees Celsius.
Control band settings, for the detection of out-of-control situations, used by Auto-Batch to decide to abort, or not start the batch.
Temperature Control Valve tuning. To configure the PID control loop.
A enable/disable temperature control setting. Disabled if an external temperature controller is desired.
g. Stabilization
Pressuring cell pressure control. The value which is applied to the cell source control valve during pressure ramp.
Scan Pressure Target. Target value in torr, target which the PID controls the cell pressure, through the cell vent variable control valve.
Batch Scan Type. Options are Bleed-Through or static. The only option currently valid is Bleed-Through.
Vent Control Settings. A collection of values, which the PID control loop uses to control the cell vent valve and determine its stability, during stabilization of an applied source gas.
Environics Control Settings. Same purpose as the Vent Control Settings, but for the condition of the source gas is provided through the Environics gas divider. Needs different settings, due to the wide gap in gas flows, from divided vs non-divided gases of all types.
h. AutoFTIR States
Vent timeout. The quantity in seconds, which is used for the timeout period of a system manifold vent sequence.
Vent enable. Enables or disables the system vent sequence in an AutoBatch test.
DB Debug mode. Enables or disables debugging of all database sql statements. Logs debugging information to the database.

Auto Set N2 purge. Enables or disables the AutoBatch to automatically set the N2 purge during an AutoBatch routine.

Use Quant Files. Enables or Disables the use of Quantification files for the quantification of a concentration from Omnic.

Disabling this uses an obsolete method for analysis of the spectral file.

Error Logging. Enables or disables error logging to the database, during an AutoBatch test.

Base Path. The installation path of the AutoFTIR software. Enables the software to be installed anywhere.

IO IP Address. The ip address of the Automation Direct IO, to which the AutoFTIR software communicates, through Modbus protocol.

Omnic Timeout. The quantity in seconds, which the AutoFTIR software flags the Omnic interface as dead. Will abort an auto-batch if a timeout condition occurs. Also, AutoFTIR notifies the user of the timeout condition, through the Dialog subtab in the AutoBatch GUI.

i. Gas Mapping

Maps the Component Range table to the divider gas library. The Batch Builder then use a gas mapping in the building of auto-batches.

Add a map entry.

Delete a map entry.

j. FTIR Setup

General settings for the configuration of the Omnic software.

Includes bench and experiment file settings.

Figure 8:
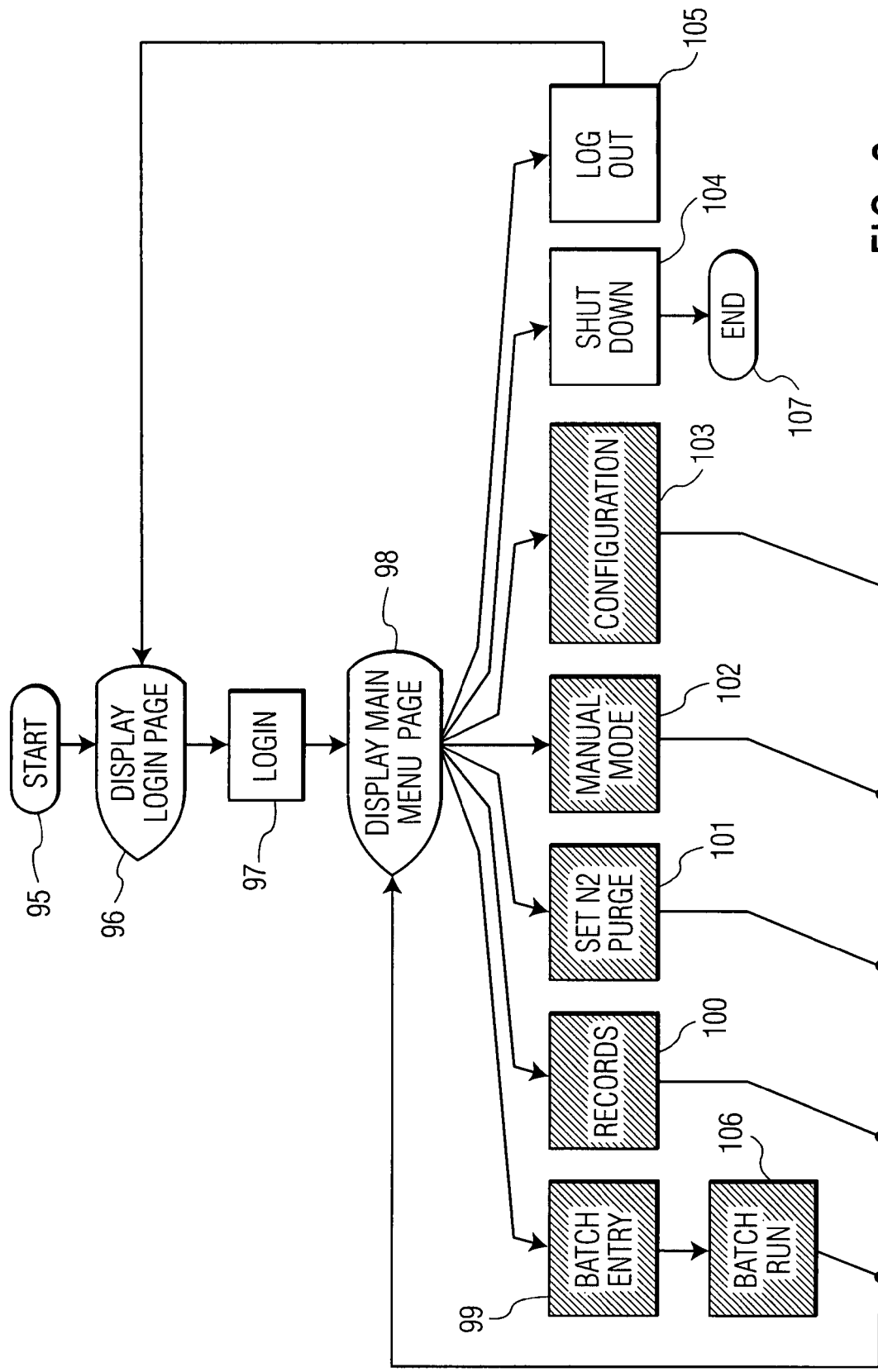
FIG. 8 is a flow diagram showing a method for controlling various application programs executed by the computer of the system shown in FIGS. 1A-1C, in accordance with an embodiment of the present invention.

Referring to FIG. 8, there is shown a top level block diagram of some of the program applications executed by host/computer/server 21. As shown, upon initialization of the system in step 95, the user is provided with a display login page 96. By using an appropriate user authentication, the user may login during step 97. Upon login, the system displays the main page menu 98 on screen 20 to the user. The main page menu is used to navigate to different parts of the application. These applications include batch entry 99, records 100, setting nitrogen purge 101, manual mode 102, configuration 103, shutdown 104 and logout 105. These applications are described below.

The batch entry 99 permits the user to configure the parameters relevant to the analysis required for a particular batch test. The batch entry provides the user a sample view, which allows the user to enter variables associated with the gas sample cylinders. Batch entry also provides a standard view, which allows the user to enter variables associated with the gas standard cylinders. The application also provides a display zero view, which allows the user to enter variables associated with the zero gas.

Batch run 106 is the application entered by the system after batch entry is completed. The batch run performs analysis and data collection of the tests. Records 100 allows access by the user to previous batches stored in database 21a. The set nitrogen purge application is activated by the user to purge system 10. The manual mode allows the user to manually operate the various discrete valves and control valves, to manipulate the FTIR module, and to view various transducer readings. The configuration application provides several options to the user to set system variables, manage user access and configure the FTIR module settings. These applications are described in more detail below.

The set N2 purge 101 checks the lines with the gas supplied from the target cylinders. The N2 purge may be restricted to the each line supplied with an open cylinder on that line. By setting the N2 purge on unused lines, however, the cylinder connection lines may be protected from contamination of the atmosphere. The N2 purge may be set manually or automatically after every batch. This is an important feature, because it minimizes the time that an unconnected cylinder connection may be exposed to the atmosphere.

The manual mode 102 presents the user with interactive graphics which represent every important aspect of the system. The manual mode enables the user to utilize the system for non-AutoBatch applications. It also may be used as a hardware debugging tool to find leaks and other problems.

Figure 9:
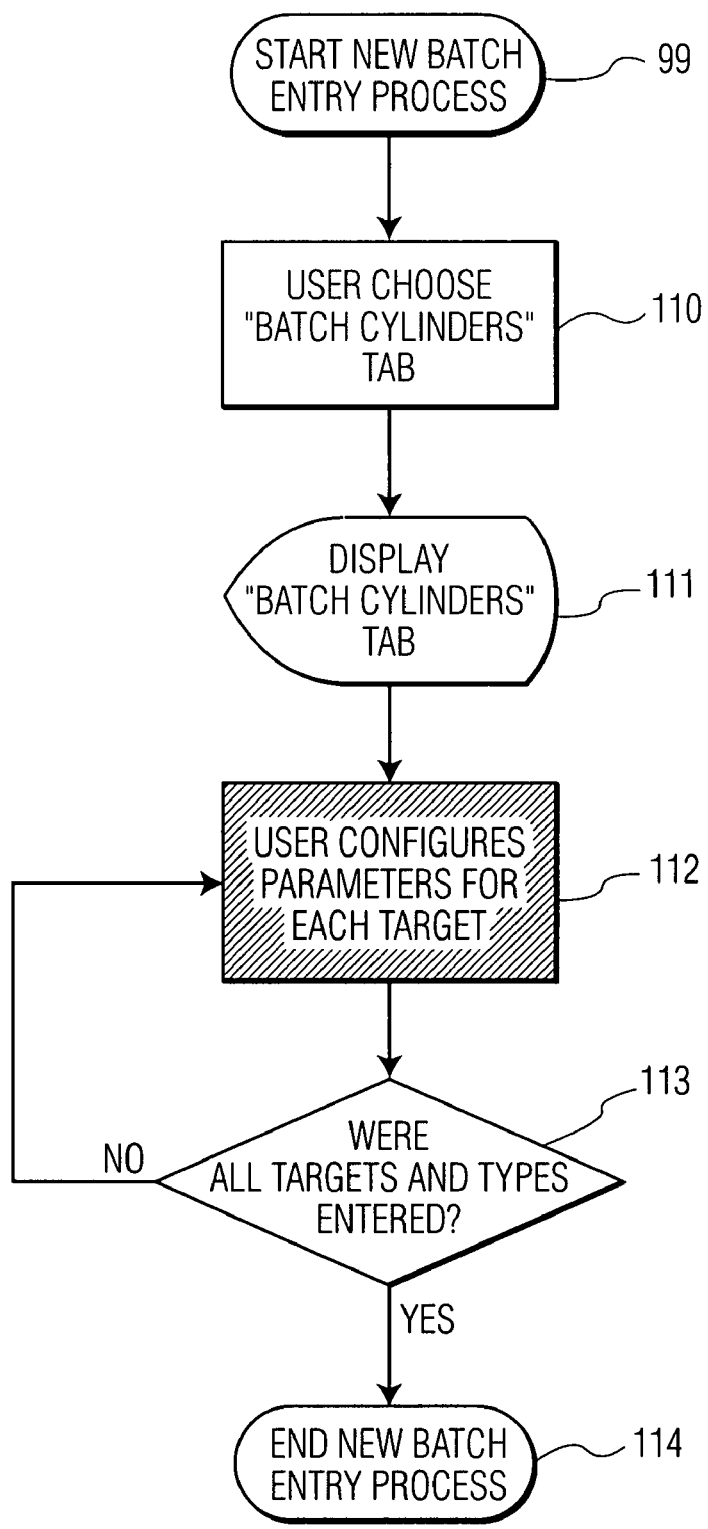
FIG. 9 is a flow diagram showing a method of a batch entry, in accordance with an embodiment of the present invention.

The batch entry 99 is shown in greater detail in FIG. 9. As shown, the user chooses the batch cylinders tab on the screen in step 110. The system then displays the batch cylinders tab in step 111. The user may now configure the parameters for each target cylinder included in the batch (step 112). By using the batch cylinders tab, the user enters data, such as cylinder number, vacuum level, etc. The parameters that may be configured by the user for each target include variables associated with the sample gas cylinders, the standard gas cylinders, and the zero gas cylinder. For the sample cylinders provided in the batch, the user may select the analysis type to be performed on each target cylinder. Such analysis includes the curve generation, described above, which may be executed once for each target cylinder. Another analysis type, also described above, is analysis that causes the batch to sample the three triads in sequence.

The user is queried on the menu whether gas divider 12 is to be used in the present batch. If the gas divider is not being used, then the user may move forward in the test sequence. If the gas divider is used, however, the user needs to first set various parameters associated with the gas divider.

Continuing the description of FIG. 9, decision box 113 determines whether all targets and types have been entered. If the answer is yes, then the method branches to end the batch entry process (step 114). Otherwise, if the answer is no, the method branches back to step 112 to complete configuration parameters for all the other targets.

The batch entry provides three views to the user, namely batch summary, batch saves and batch entry. The batch entry enables the user to configure the AutoBatch function. The batch summary concisely displays to the user all the batch configuration parameters. This is important, because it allows the user to review the batch configuration before starting a batch test. Lastly, the batch saves provides the user with a save batch, load batch and delete batch functions. It lists all the batches that are saved. This is an important feature, because it permits the user to replicate a batch test, without the user having to spend a great deal of time entering data for large batches. It also permits the saving of a batch, in case of an AutoBatch failure. The user may recall a batch through his batch edit function, or may restart the batch without retyping previously entered data.

Figure 10:
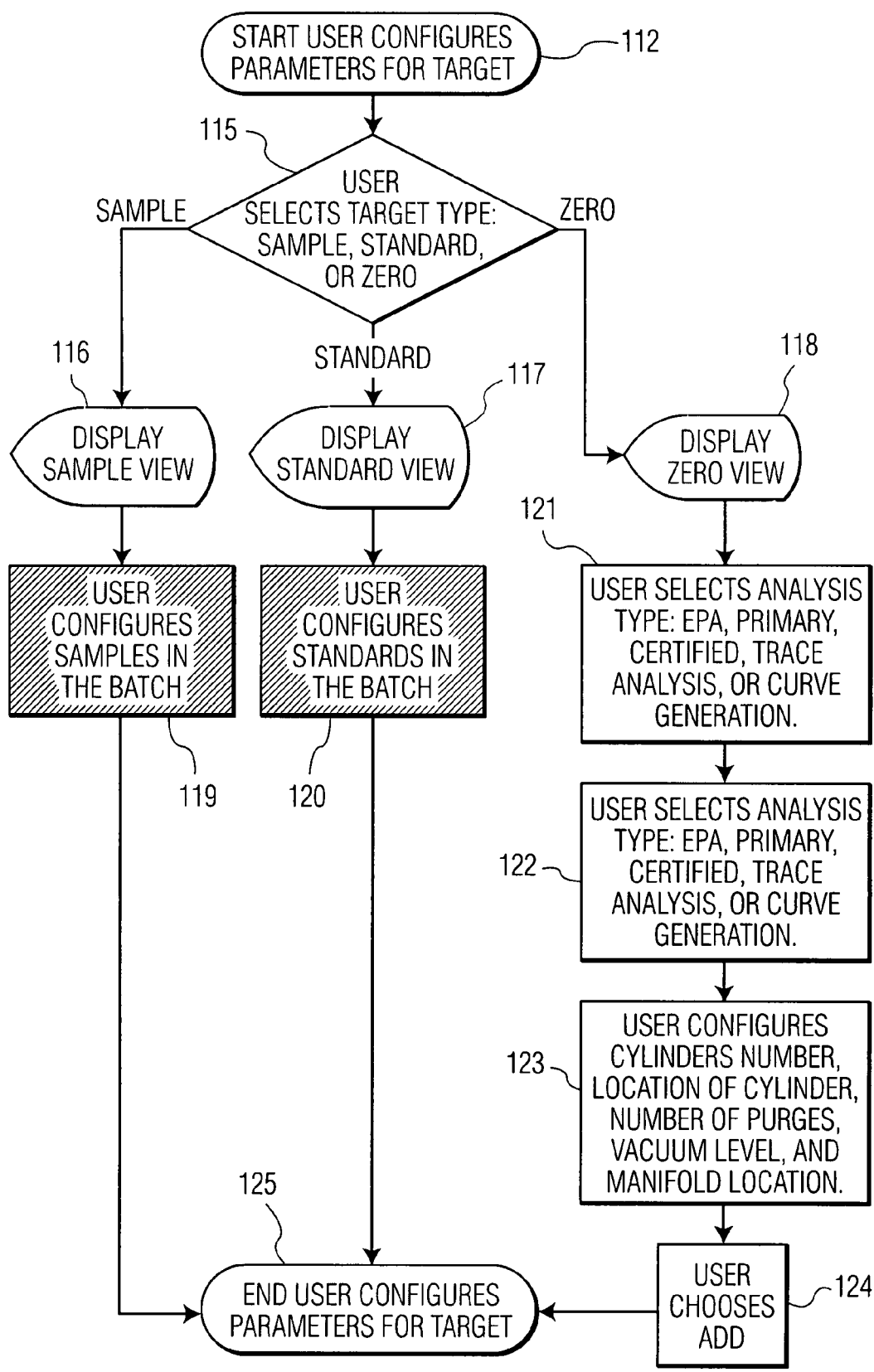
FIG. 10 is a flow diagram showing a method of configuring parameters for a target gas, in accordance with an embodiment of the present invention.

The method in which the user configures parameters for each target cylinder (referred to as step 112) is shown in detail in FIG. 10. As shown, the user selects the target type as either sample, standard, or zero (step 115). If the user selects target type sample, the method displays the sample view in step 116. If the user selects target type standard, the method displays the standard view in step 117. Lastly, if the user selects target type zero, the method displays the zero view in step 118.

If the display shows the sample view, the user is permitted to enter variables associated with the sample gas cylinder in the batch (step 119). If the display shows the standard view, step 120 permits the user to configure the variables associated with the standard cylinders in the batch. If the display shows the zero view, the user is permitted to select various parameters in steps 121, 122 and 123. These parameters include the type of analysis to be performed on the target cylinder, namely, whether the desired analysis is to certify a target gas, whether the desired analysis is to provide curve generation. The user may also select the cylinder number, the location of the cylinder, the number of purges required for each cylinder under test, the vacuum level required, and the manifold location associated with each cylinder. After the information is provided by the user on the menu, the user may choose to push "add" at the bottom of the screen, in order to store the data and move on to the next target. The "add" function is performed in step 124. Lastly, the user ends method 112 in step 125.

Figure 11:
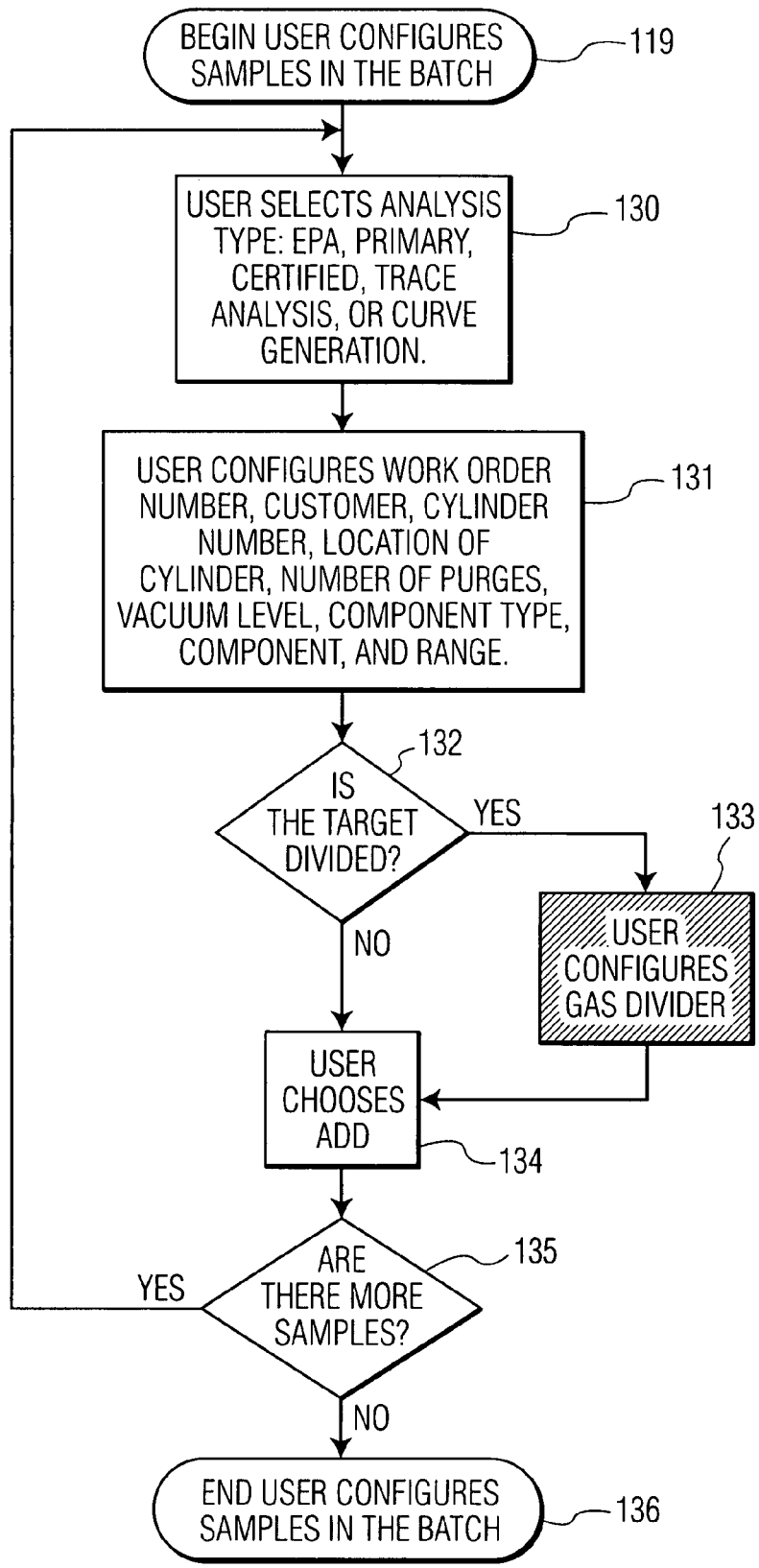
FIG. 11 is a flow diagram showing a method of configuring samples in a batch, in accordance with an embodiment of the present invention.

Greater detail of the user configures samples in the batch, generally designated as method 119, is shown in FIG. 11. As shown, step 130 permits the user to select the type of analysis to be performed on the sample gas cylinder. Such analysis may be a certification of a sample cylinder, a trace analysis of the sample cylinder, or a curve generation for the sample cylinder. Step 131 permits the user to configure the work order number of the batch, the customer, the cylinder number, location of the cylinder, number of purges desired, the vacuum level, component type and component range. After configuration of the samples, decision box 132 requires the user to determine whether the target sample cylinder is to have the gas divided. If the answer is yes, the method branches to step 133 and requires the user to configure the gas divider. The user may now set the parameters for the gas divider. If the target is not to be divided, the method branches to step 134 and allows the user to choose "add". As described before, the user pushes "add" on the screen to store the data and move on to the next target cylinder. Next, decision box 135 determines if there are any more sample cylinders in the batch. If the answer is yes, the method loops back to the beginning of step 130 and permits the user to again enter the configuration data for the next target cylinder. After all the sample cylinders are configured, the method branches to step 136 to end method 119.

Figure 12:
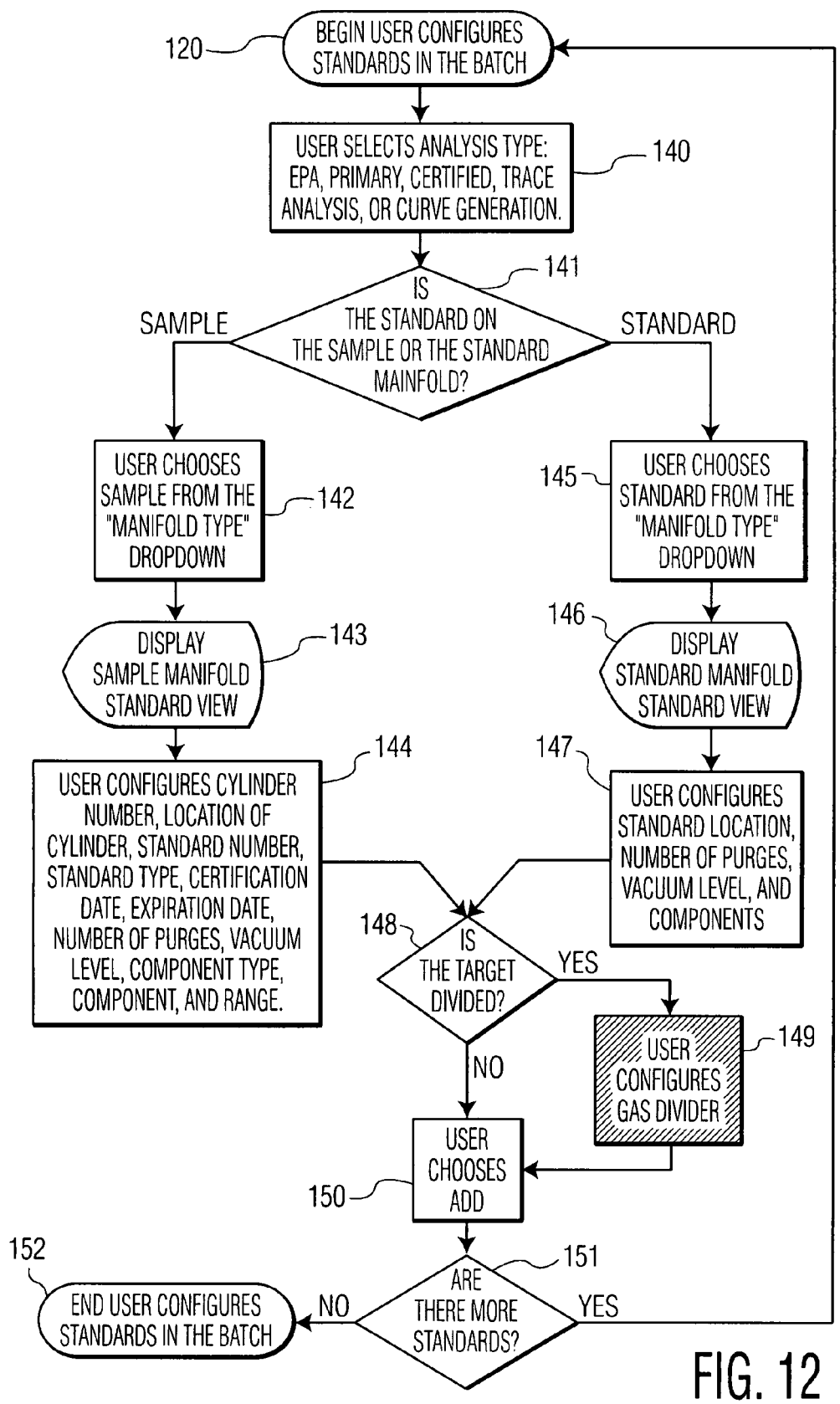
FIG. 12 is a flow diagram showing a method for configuring standards in a batch, in accordance with an embodiment of the present invention.

Greater detail of the user configures standards in the batch (step 120) is shown in FIG. 12. As shown, step 140 permits the user to select the type of analysis to be performed on the standard gas cylinder. After the user selects the analysis type, the method enters decision box 141. The user may select either sample or standard. If sample is selected by the user in step 142, the method displays the sample manifold standard view (step 143). The user may then configure the number of cylinders, the location of the cylinders, the standard number, the standard type, the certification date, expiration date, number of purges, vacuum level, component type, component and range (step 144).

If the user, on the other hand, selects standard from the manifold type drop down (step 145), the method, using step 146, displays the standard manifold standard view. With step 147 the user may configure the system for the standard location, number of purges desired, vacuum level, and the components.

It will be appreciated that by configuring the standards within the configuration process and storing the configuration in the database, the present invention reduces the number of steps required to otherwise configure an AutoBatch process. This saves process time, reduces user efforts, reduces movements of the gas cylinders, and reduces mistakes. The user may recall the standard gas positions, thereby allowing the system to auto-populate the standard information required for a batch, without any user interaction. This saves process time, and reduces user efforts.

The method also checks the user's batch entry for possible mistakes before starting a batch run. This reduces the quantity of aborted batches, saves time and saves gas consumption.

One example of a possible mistake that is checked by the method is a missing reference gas of a component in an EPA analysis. An alert of such missing reference is provided to the user by the method of the invention.

Another advantage of the present invention is that a batch configuration may be recalled by the user. This saves the user data entry time for repeated batches, or similar batches.

As described later, the user may also set the number of purges and vacuum level on a per target basis. This is advantageous for problematic analyzes and expands the applicability of the AutoFTIR system to a larger set of possible analyzes.

The method also provides filtering options based on the standards chosen by the user. This reduces mistakes and effort in entering batch data, by constraining the large number of possible components to actual components chosen in the standards that have been configured.

Based upon the user specified component and range, the method advantageously eliminates curve selection errors and reduces the need for manual recalculation of the spectral files, when discrepancies occur.

The present invention also allows the user to set up a batch test and then schedule the batch test to start at a future time. This facilitates testing during a period of low user attendance, such as attendance during the weekend, or overnight.

Returning to FIG. 12, the method alerts the user as to whether the target is to be divided or not divided (decision box 148). If the target is to be divided, then the method branches to step 149 and allows the user to configure the gas divider. The method then branches to step 150, where the user may choose "add". Pushing "add" allows the user to store the data and move on to the next target. The method, using decision box 151, determines whether there are any more standards to be configured. If the answer is yes, the method branches back to step 140. If there are no more standards to be configured, on the other hand, the method branches to step 152 and ends method 120.

Figure 13:
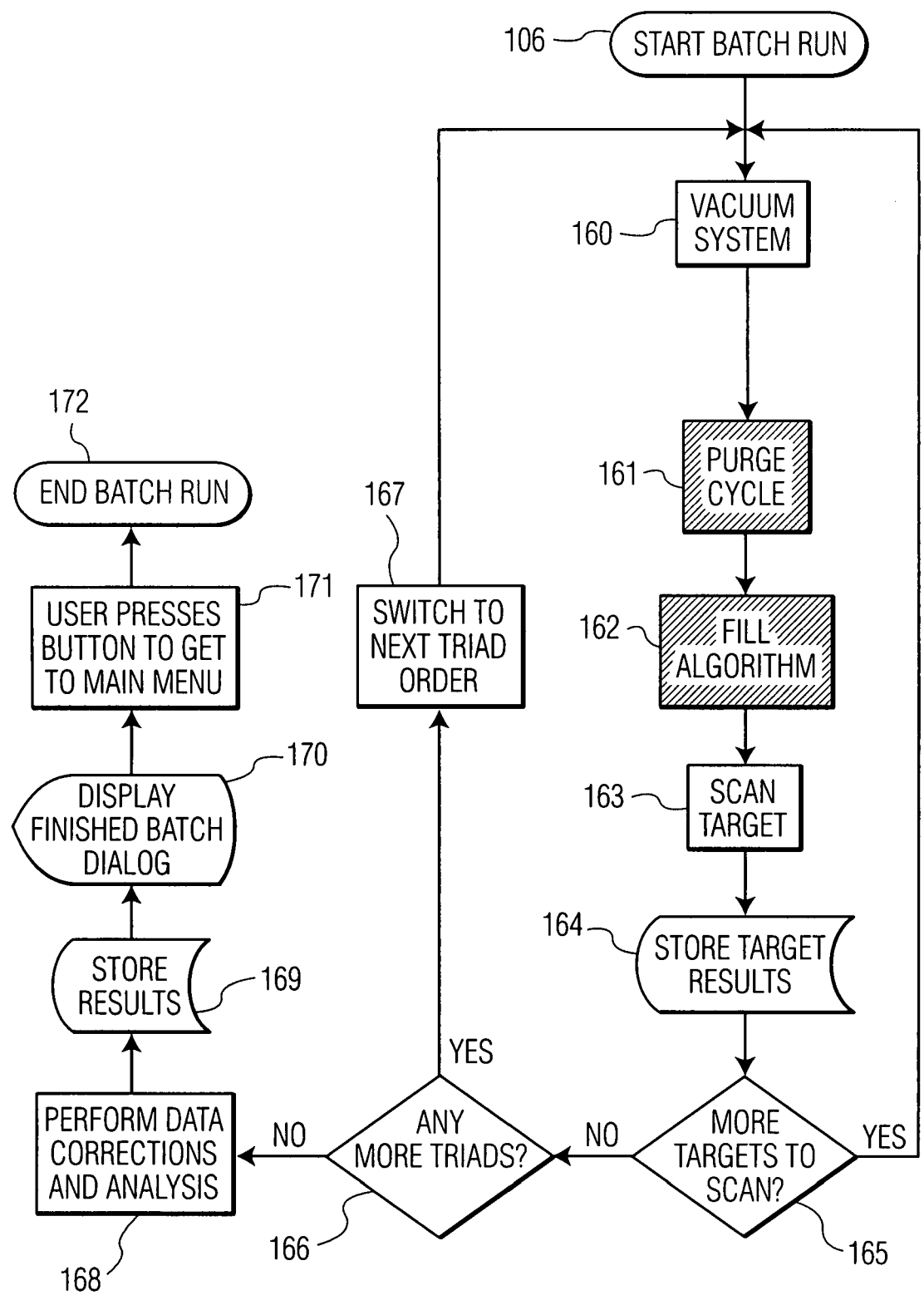
FIG. 13 is a flow diagram showing a method for performing a batch run, in accordance with an embodiment of the present invention.

The start batch run 106 (shown in FIG. 8) will now be described in greater detail with respect to FIG. 13. As shown in FIG. 13, the method starts the batch run by vacuuming the system in step 160. Next, the method performs a purge cycle (step 161 and executes the fill algorithm (step 162). The purge cycle and the fill algorithm are described in greater detail later. After filling the gas cell and executing the fill algorithm, the method scans the target in step 163, using the FTIR module. Results of the scan are stored in step 164.

Next, decision box 165 determines whether there are any more targets to scan. If there are more targets to scan, the method branches back to step 160 and begins another vacuum and purging cycle. If there are no more targets to scan, the method branches to decision box 166 to determine whether there are any more triads. If there are more triads, step 167 switches to the next triad, allowing the method to begin another vacuum cycle in step 160. If there are no more triads remaining, the method branches to step 168 and performs data corrections and analysis on the target results. Results of the corrections and analysis are stored by step 169 into the database. The method, in step 170, displays to the user that the batch run is completed. The user may then press a button to get to the main menu (step 171) and end the batch run (step 172).

Greater detail of the purge cycle (step 161) will now be described by reference to FIG. 14. As shown, decision box 175 determines whether the vacuum level of the system is less than a predetermined vacuum setting. If the vacuum level is less than the predetermined vacuum setting, the method branches to step 176 and begins opening the target cylinder to fill the gas cell to the configured pressure. Decision box 177 is entered next to determine whether the number of purges are equal to the preset number of purges desired (usually 2 purges). If the answer is no, the method branches to step 178 and performs another cell purge. At the end of the cell purge, decision box 179 determines whether the cell pressure is now greater than the set purge pressure. If the cell pressure is greater, the method branches back to begin another purge cycle. If the cell pressure is less than the set purge pressure, the method branches to step 181 to abort the procedure, upon expiration of a timeout. The purge cycle ends at step 180.

Figure 14:
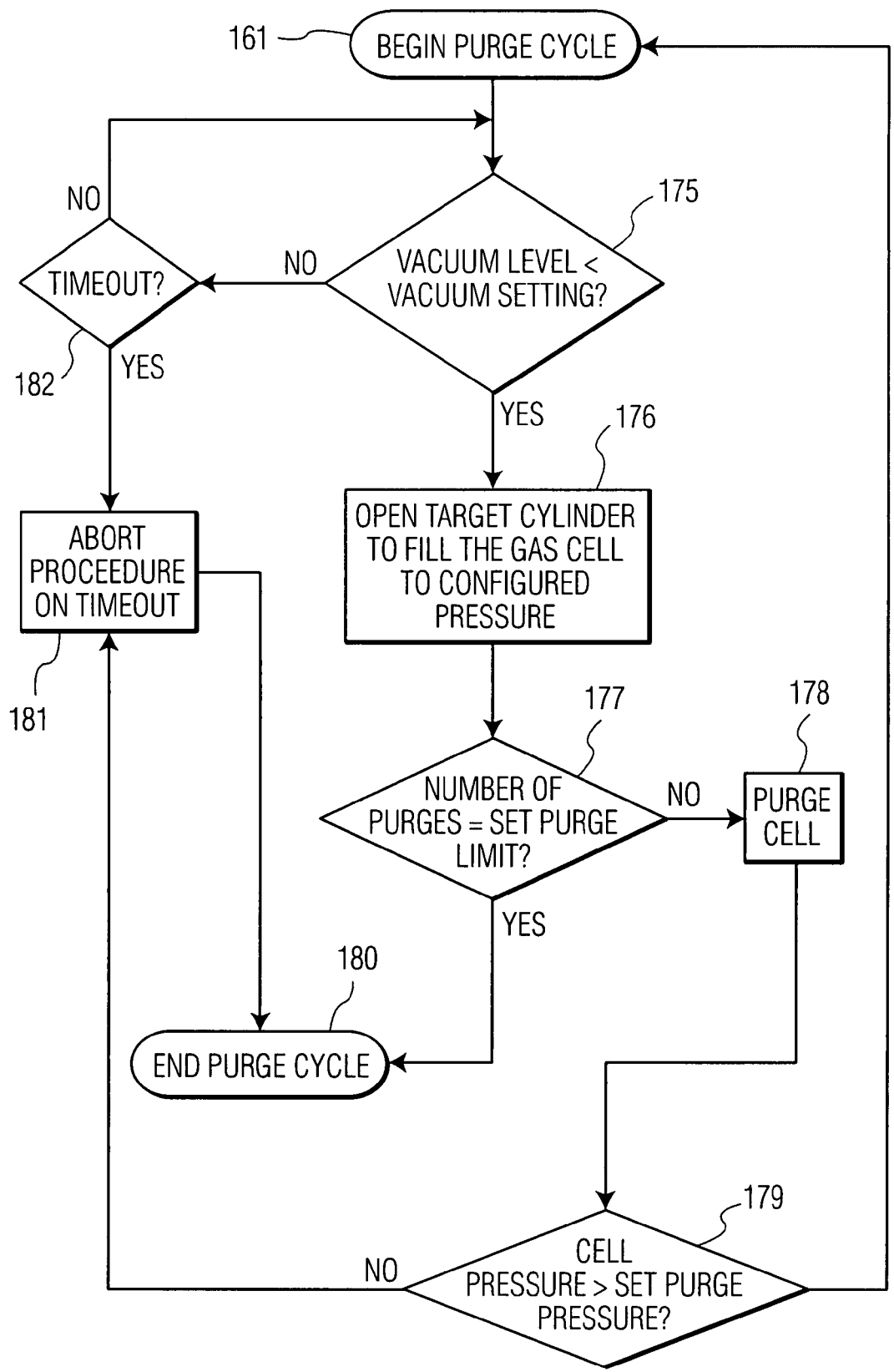
FIG. 14 is a flow diagram showing a method for purging the system of the present invention.

Referring back to decision box 175 in FIG. 14, if it is determined that the vacuum level is greater than or equal to the vacuum setting, the method branches to decision box 182 and performs a timeout. Once the timeout is reached, the method aborts the purge cycle (step 181) and ends the purge cycle (step 180).

Figure 15:
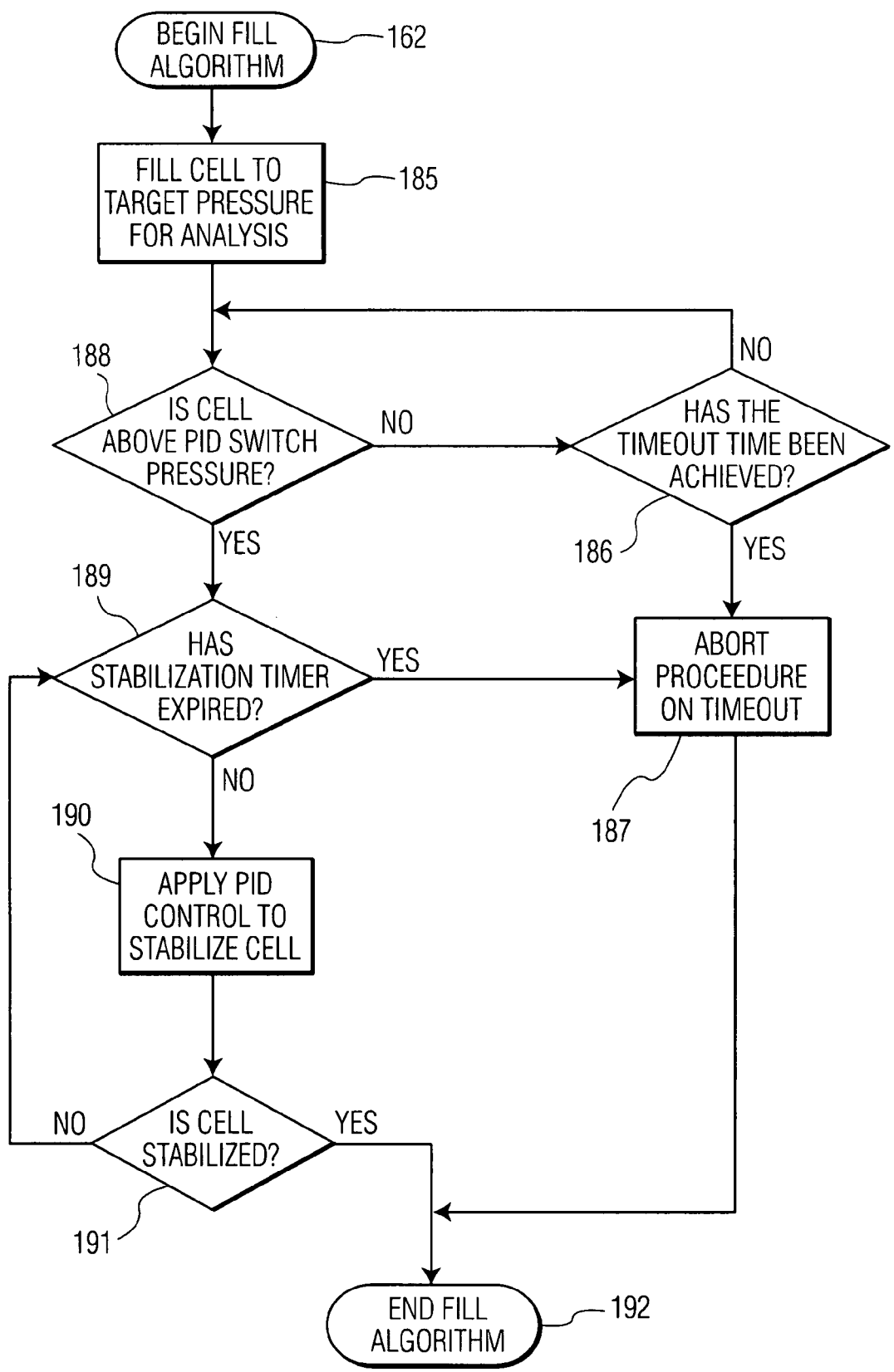
FIG. 15 is a flow diagram showing a method for executing a fill algorithm by the computer of the present invention.

The fill algorithm (step 162) shown in FIG. 13 will now be described in greater detail by reference to FIG. 15. As shown, the method begins filling the gas cell to the target pressure for scanning and analysis (step 185). The method enters decision box 188 and determines whether the cell pressure is above the PID switch pressure. If the cell pressure is above the PID switch pressure, the method branches to step 189. A stabilization timer is started by decision box 189. The method then determines whether the stabilization timer has expired. If the stabilization timer has not expired, the method branches to step 190 and applies the PID program control, described before, to fine-tune the gas cell.

The method next determines whether the gas cell is stabilized to the desired pressure (decision box 191). If the gas cell is stabilized, the fill algorithm is ended in step 192. Different timeouts are included in the method, as shown in FIG. 15. A first timeout is used by decision box 186. If the gas cell does not reach a pressure above the PID switch pressure level, decision box 186 branches to step 187 and aborts the procedure. A second timeout is used by decision box 191. If the gas cell is not stabilized before the timeout expires, the method again branches to step 187 and aborts filling of the gas cell.

Figure 16:
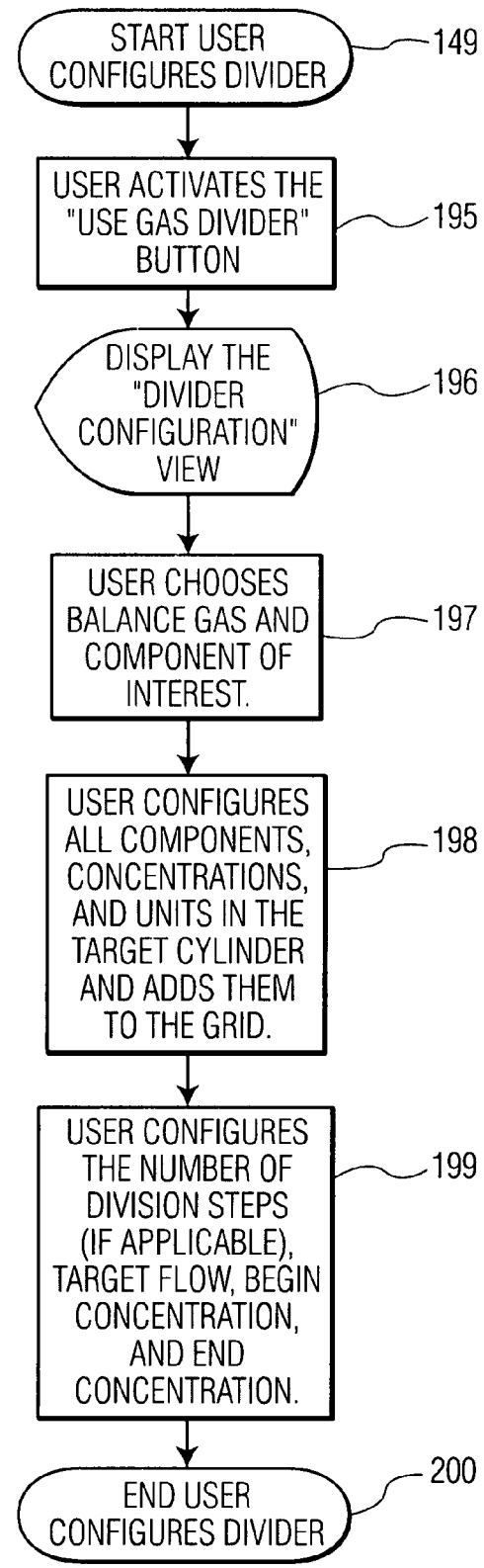
FIG. 16 is a flow diagram showing a method for configuring the gas divider of the system in FIG. 1A, in accordance with an embodiment of the present invention.

Configuration of the gas divider (step 149), first shown in FIG. 12 will now be described in detail with respect to FIG. 16. As shown, the method requests the user to activate the "use gas divider" button (step 195) and displays the divider configuration view to the user (step 196). The user chooses the balance gas and the component of interest in order to dilute the sample gas (step 197). Using step 198, the user is allowed to configure the components, concentrations and units in the target cylinder. The method next alerts the user (step 199) to configure the number of division steps (if necessary), the target flow, the beginning concentration level and the ending concentration level. Step 200 ends the procedure.

Figure 17:
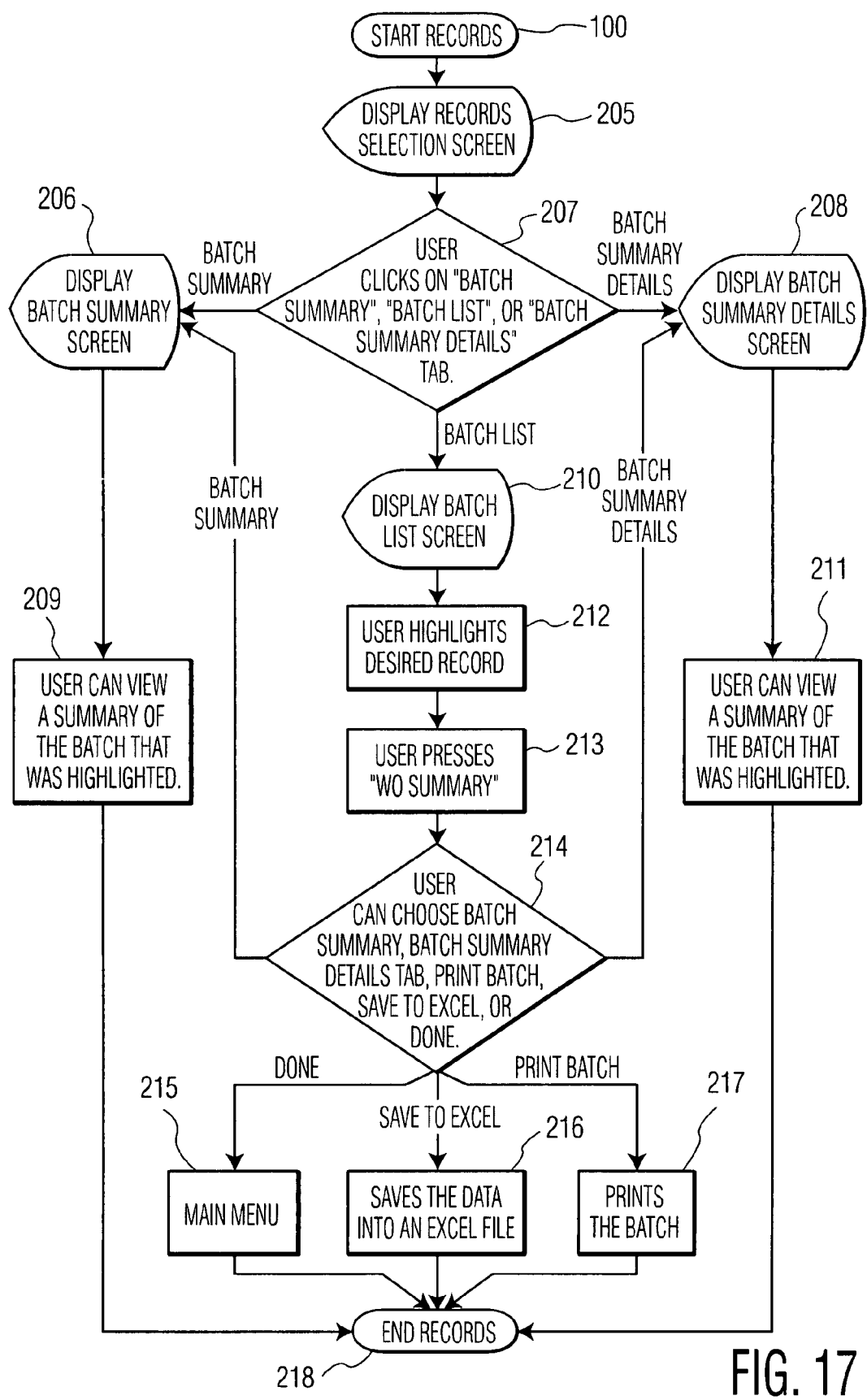
FIG. 17 is a flow diagram showing a method for executing the records application as a method of the present invention.

The method for implementing the records (step 100), first shown in FIG. 8, will now be described in greater detail by reference to FIG. 17. As shown, the method displays the records selection screen to the user (step 205). The user may either choose "batch summary", "batch summary details", or "batch list", as shown in decision box 207. If the "batch list" is chosen, step 210 displays the batch list screen and the user in step 212 highlights the desired record. Step 213 allows the user to select the work order summary, and the method branches to decision box 214. Decision box 214 permits the user to choose "batch summary", in which case the method branches to step 206. The user may also choose "batch summary details", in which case the method branches back to step 208. Lastly, the user may print the batch, or save the records to excel (decision box 214).

If step 206 is entered, the method displays the "batch summary" screen and permits the user to view the summary of the batch on the screen (step 209). If "batch summary details" is selected, the method provides the user the "display batch summary details" screen (step 208) and permits the user to view the summary of the batch (step 211). If "saved to excel" is selected by the user (decision box 214), the method branches to step 216 and saves the data into an excel file. The start records program is ended in step 218. The user may also branch back to the main menu in step 215, or print the batch by branching to step 217.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for certifying to a user a concentration of gas in a cylinder comprising:
   a gas cell configured to receive a sample gas from a cylinder,
   an FTIR (Fourier Transform Infrared) spectrometer coupled to the gas cell for scanning the sample gas and forming a beam spectrum,
   a processor coupled to the FTIR spectrometer for calculating an intensity response of the sample gas based on the beam spectrum,
   a storage device for storing data points of a plot of intensity response of a known gas versus concentration levels,
   wherein the processor is configured to interpolate between the stored data points of the plot to determine an interpolated data point corresponding to a resultant intensity response of the sample gas, and
   provide to the user a concentration level of the sample gas based on the interpolated data point,
   the gas cell configured to receive a standard gas from a cylinder and a zero gas from another cylinder,
   the FTIR spectrometer configured to scan the standard gas and the zero gas, and the processor configured to calculate an intensity response of the standard gas and an intensity response of the zero gas,
   wherein the intensity response of the sample gas is Xn, the intensity response of the standard gas is Yn, and the intensity response of the zero gas is Zn, and
   the resultant intensity response of the sample gas is based on the following equation:

$$Rn = \left(\frac{Ya}{Yn - Zn}\right)Xn - \left(\frac{Ya}{Yn - Zn}\right)Zn$$

where:
   Xn is the sample intensity response,
   Yn is the standard intensity response,
   Ya is the actual value of the standard gas provided as an input value by the user,
   Zn is the zero intensity response,
   n is a scan number (n is 1 or greater), and
   Rn is the resultant intensity response of the sample gas.

2. The system of claim 1 wherein
   the processor is configured to execute an integration algorithm for determining an area of at least one region of the beam spectrum, and provide the determined area as the intensity response of the sample gas.

3. The system of claim 2 wherein
the storage device includes data points of a plot of area versus concentration levels of the known gas.

4. The system of claim 3 wherein
the processor includes a curve fitting algorithm for finding data points of the intensity response of the known gas versus concentration levels, based on a plurality of scans performed by the FTIR spectrometer on a corresponding plurality of cylinders each containing the known gas, and
the processor is configured to store the data points in the storage device as the plot of intensity response of the known gas versus concentration levels.

5. The system of claim 4 wherein
the curve fitting algorithm depends on at least ten scans performed by the FTIR spectrometer on a corresponding ten cylinders containing the known gas.

6. The system of claim 4 wherein
the curve fitting algorithm uses at least one of a linear, quadratic, cubic or quartic orders of a polynomial equation.

7. The system of claim 1 including
a valve disposed at an output port of the gas cell,
the valve adaptively tunable to vent the gas from the output port,
wherein the processor includes an algorithm to tune the valve to vent the gas at a predetermined pressure level, and
the FTIR spectrometer begins scanning the sample gas after the algorithm tunes the valve to vent at the predetermined pressure level.

8. A system for certifying to a user a concentration of gas in a cylinder comprising:
a gas cell configured to receive a sample gas from a cylinder,
an FTIR (Fourier Transform Infrared) spectrometer coupled to the gas cell for scanning the sample gas and forming a beam spectrum,
a processor coupled to the FTIR spectrometer for calculating an intensity response of the sample gas based on the beam spectrum,
a storage device for storing data points of a plot of intensity response of a known gas versus concentration levels,
wherein the processor is configured to interpolate between the stored data points of the plot to determine an interpolated data point corresponding to a resultant intensity response of the sample gas, and
provide to the user a concentration level of the sample gas based on the interpolated data point,
the gas cell is configured to receive a standard gas from a cylinder and a zero gas from another cylinder,
the FTIR spectrometer is configured to scan the standard gas and the zero gas,
the processor is configured to calculate an intensity response of the standard gas and an intensity response of the zero gas, and
the resultant intensity response of the sample gas is calculated based on a sequence of first, second and third tests;
wherein the first test includes a scan order of scanning first the zero gas, second the standard gas, and third the sample gas, and then computing a first correction,
the second test includes a scan order of scanning first the standard gas, second the zero gas, and third the sample gas, and then computing a second correction,
the third test includes a scan order of scanning first the standard gas, second the sample gas, and third the zero gas, and then computing a third correction, and
the resultant intensity response is based on the first, second and third corrections.

9. The system of claim 8 wherein the first, second and third tests are performed in any sequence.

10. A system for certifying to a user a concentration of gas in a cylinder comprising:
a gas cell configured to receive a sample gas from a cylinder,
an FTIR (Fourier Transform Infrared) spectrometer coupled to the gas cell for scanning the sample gas and forming a beam spectrum,
a processor coupled to the FTIR spectrometer for calculating an intensity response of the sample gas based on the beam spectrum,
a storage device for storing data points of a plot of intensity response of a known gas versus concentration levels,
wherein the processor is configured to interpolate between the stored data points of the plot to determine an interpolated data point corresponding to the intensity response of the sample gas, and
provide to the user a concentration level of the sample gas based on the interpolated data point,
a gas divider is disposed between the gas cell and the cylinder for diluting the concentration of the sample gas in the cylinder, and
when the sample gas in the cylinder has a concentration level greater than the concentration levels of the known gas stored in the storage device, then the gas divider is configured to dilute the sample gas before scanning.

* * * * *